United States Patent
Bordat et al.

(10) Patent No.: US 8,420,610 B2
(45) Date of Patent: Apr. 16, 2013

(54) POLYUNSATURATED COMPOUNDS, METHOD FOR PREPARING SAME AND COMPOSITIONS CONTAINING THE SAME

(75) Inventors: Pascal Bordat, Mervilla (FR); Roger Tarroux, Toulouse (FR); Jean-Hilaire Saurat, Geneve (SE); Olivier Sorg, Geneve (SE); Jean-Louis Brayer, Nanteuil le Haudoin (FR); Natacha Frison, Creil (FR)

(73) Assignee: Pierre Fabre Dermo-Cosmetique, Boulogne-Billancourt (FR)

( * ) Notice: Subject to any disclaimer, the term of this patent is extended or adjusted under 35 U.S.C. 154(b) by 831 days.

(21) Appl. No.: 12/086,625

(22) PCT Filed: Dec. 14, 2006

(86) PCT No.: PCT/EP2006/069731
§ 371 (c)(1),
(2), (4) Date: Jun. 16, 2008

(87) PCT Pub. No.: WO2007/068745
PCT Pub. Date: Jun. 21, 2007

(65) Prior Publication Data
US 2010/0168045 A1    Jul. 1, 2010

(30) Foreign Application Priority Data

Dec. 14, 2005  (FR) ..................................... 05 12661

(51) Int. Cl.
*A01N 43/04*    (2006.01)
*A01N 37/00*    (2006.01)
*A61K 31/70*    (2006.01)
*A61K 31/19*    (2006.01)
*C07H 15/00*    (2006.01)
*C07C 59/00*    (2006.01)

(52) U.S. Cl.
USPC ............... 514/35; 514/557; 536/4.1; 554/213

(58) Field of Classification Search .................. None
See application file for complete search history.

(56) References Cited

U.S. PATENT DOCUMENTS

| | | | |
|---|---|---|---|
| 3,068,257 | A | 12/1962 | Entschel et al. |
| 3,311,656 | A | 3/1967 | Surmatis et al. |
| 5,962,534 | A | 10/1999 | Gudas et al. |
| 6,818,657 | B1 | 11/2004 | Redoules et al. |
| 7,265,143 | B2 | 9/2007 | Njar et al. |

FOREIGN PATENT DOCUMENTS

| | | |
|---|---|---|
| FR | 2 791 679 A | 10/2000 |
| VA | 2004-509073 A | 3/2004 |
| WO | WO-02/03912 A | 1/2002 |

OTHER PUBLICATIONS

Kaderavek et al., Czechoslovak Journal of Physics, vol. 56, 2006, suppl. D, pp. D711-D717.*
Katsuta et al., J. Org. Chem., 1994, vol. 59, pp. 6917-6921.*
Balogh-Nair et al., "The 'Opsin Shift' in Bacteriorhodopsin: Studies with Artificial Bacteriorhodopsins", Photochemistry and Photobiology, vol. 33 (1981) pp. 483-488.
Curley et al., "4-Oxygenated Retinoids: Unexpected Chemopreventive Potential for Analogues Originally Synthesized as Affinity Labels", Bioorganic & Medicinal Chemistry Letters, vol. 2, No. 9 (1992) pp. 1133-1136.
Entschel et al., "Synthesen von 4-Hydroxyderivaten von β-Apo-carotinalen und β-Apo-carotinsäuren sowie Darstellung von 3,4-Dehydro-β-apo-carotinalen and 3,4-Dehydro-βapo-carotinsäuren", Helvetica Chimica Acta, vol. 43 (1960) pp. 94-101.
Excerpt from the Bioorganicheskaya Khimiya, vol. 7, No. 11 (1981) pp. 1731-1733.
Katsuta et al. "Synthesis of (+)-(4S)- and (-)-(4R)-11Z-4-Hydroxyretinals and Determination of the Absolute Sterochemistry of a Visual Pigmant Chromophore in the Bioluminescent Squid, *Watasenia scintillans*", Tetrahedron Letters, vol. 35, No. 6 (1994) pp. 905-908.
Rosenberg, "Retinoic Acid Metabolites. 1. Total Synthesis of 4-Hydroxy- and 4-Oxoretinoic Acid", J. Org. Chem., vol. 47 (1982) pp. 1698-1701.
Samokyszyn et al., "4-Hydroxyretinoic Acid, A Novel Substrate for Human Liver Microsomal UDP-glucuronosyltransferase(s) and Recombinant UGT2B7", J. Biological Chemistry, vol. 275, No. 10 (2000) pp. 6908-6914.
Translation of Japanese Office Action issued in Japanese patent application No. 2008-545006 on Jul. 3, 2012.

* cited by examiner

*Primary Examiner* — Traviss C McIntosh III
(74) *Attorney, Agent, or Firm* — Birch, Stewart, Kolasch & Birch, LLP.

(57) ABSTRACT

The invention concerns novel polyunsaturated compounds of formula (I) wherein: $R_1$ represents a $R'_1$, -A-$R'_1$ group, $R'_1$ being selected from —COOH, —$COOR_3$, —$CONH_2$, —$CONHR_3$, —$CONR_3 R_4$, —CHO, —$CH_2OH$, —$CH_2OR_5$, and A represents a $C_2$-$C_{16}$ alkylene, alkenylene or alkynylene; $R_2$ represents: an optionally substituted aryl group or an optionally substituted heteroaryl group; a sugar residue or, a fatty acid residue optionally branched and/or substituted preferably at the chain terminus and particularly by hydroxy, acetoxy radical or by an optionally protected amino radical; a —OC —$(CH_2)$n CO-tocopheryl (alpha, beta or gamma or delta) group, with 2 $\leq$ n $\leq$ 10; a —$R'_2$—O—$R_6$ group, wherein $R'_2$ is an optionally substituted arylene group or an optionally substituted heteroarylene group, and $R_6$ represents a hydrogen atom, a straight or branched optionally substituted $C_1$-$C_{16}$ alkyl, a straight or branched optionally substituted $C_2$-$C_{16}$ alkenyl, or a straight or branched $C_2$-$C_{16}$ alkynyl group, an optionally substituted tocopheryl radical or the like, an amino acid residue, or a sugar residue. The invention also concerns the compositions, in particular cosmetic and/or dermatological compositions containing at least one compound of formula (I) as well as their use as whitening and/or depigmenting agent, and the cosmetic method using said compositions.

18 Claims, No Drawings

POLYUNSATURATED COMPOUNDS, METHOD FOR PREPARING SAME AND COMPOSITIONS CONTAINING THE SAME

The invention relates novel polyunsaturated derivatives of retinoids, methods for their preparation, compositions containing them and their use in the field of cosmetics and/or dermatology.

Retinoic derivatives are now used in dermatology in various indications such as psoriasis or ichthyosis and even skin depigmentation (reduction in melanogenesis under the effect of vitamin A).

However, the use of retinoic derivatives by topical route are involves a number of difficulties, such as a lack of stability in time and under the effect of light of these derivatives, irritation resulting from local over-concentration as well as low absorption of these derivatives through the stratum corneum. The latter disadvantage is the result of the highly lipophilic nature of the substance which, when deposited on the skin, is largely eliminated via desquamation.

The side effects, which include redness, irritation, oedema and excessive desquamation, limit the use of retinoic derivatives to patients who are highly motivated, hence the interest in improving the bioavailability of the active ingredient and its absorption at the same time as avoiding the harmful effects of local over-concentration.

The applicant has already put forward a method for overcoming the side effects of these compounds through the use of ternary glycosylated complexes offering the possibility of releasing the active substance under the effect of two enzymes (F 2 791 679). This leads to slow release which prevents the problem of accumulation.

Nevertheless, there is a need for compounds which have less problematic side effects or alternatively compounds whose greater activity would allow them to be used in lower concentrations such that the unwanted effects become less problematic.

The applicant has found that new derivatives of retinoic acid have a remarkable depigmenting action.

This invention relates compounds of formula (I):

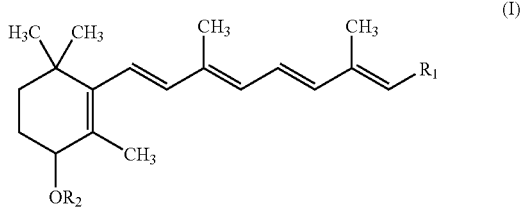

wherein $R_1$ represents a $R'_1$ or $-A-R'_1$ group in which $R'_1$ is chosen from among —COON, —COOR$_3$, —CONH$_2$, —CONHR$_3$, —CONR$_3$R$_4$, —CHO, —CH$_2$OH, —CH$_2$OR$_5$, and A represents a linear or branched $C_1$-$C_{16}$ alkylene group, linear or branched $C_2$-$C_{16}$ alkenylene group or linear or branched $C_2$-$C_{16}$ alkynylene group.

$R_2$ represents:
- an aryl group, optionally substituted, or heteroaryl group, optionally substituted, or
- an osidic residue, or
- a fatty acid residue optionally branched and/or substituted, preferably at the end of the chain and in particular by a hydroxy, acetoxy or protected or non-protected amino radical,
- an —OC—(CH$_2$)$_n$—CO-tocopheryl (alpha, beta or gamma or delta) group with $2 \leq n \leq 10$,
- an —R'$_2$—O—R$_6$ group, wherein R'$_2$ is an arylene group, optionally substituted, or a heteroarylene group, optionally substituted, and R$_6$ represents hydrogen atom, linear or branched $C_1$-$C_{16}$ alkyl groups, optionally substituted, linear or branched $C_2$-$C_{16}$ alkenyl group, optionally substituted, or linear or branched $C_2$-$C_{16}$ alkynyl group, optionally substituted, a tocopheryl radical, optionally substituted, or an analogue, an amino acid residue or an osidic residue.

$R_3$ and $R_4$ independently represent a linear or branched $C_1$-$C_{16}$ alkyl radical, optionally substituted, linear or branched $C_2$-$C_{16}$ alkenyl, or linear or branched $C_2$-$C_{16}$ alkynyl, optionally substituted.

$R_5$ represents a linear or branched $C_1$-$C_{16}$ alkyl radical, optionally substituted, linear or branched $C_2$-$C_{16}$ alkenyl group, optionally substituted, branched or linear $C_2$-$C_{16}$ alkynyl group optionally substituted or a linear or branched $C_2$-$C_{16}$ acyl group, optionally substituted, their enantiomers and diastereoisomers, as well as any salts resulting from addition to an acid or physiologically acceptable base.

Pharmaceutically acceptable acids include, in a non-limiting manner, the following acids hydrochloric, hydrobromic, sulphuric, phosphonic, acetic, trifluoroacetic, lactic, pyruvic, malonic, succinic, glutaric, fumaric, maleic, methanesulphonic, camphoric, oxalic, etc.

Pharmaceutically acceptable bases include, in a non-limiting manner, sodium hydroxide, potassium hydroxide, triethylamine, tert-butylamine, etc.

The double bonds of the unsaturated group generally all have an E configuration but this invention also relates the use of compounds of formula (I) in which all or only part of the double bond presents a Z configuration.

The term aryl refers to a phenyl, naphthyl or biphenyl group.

The term heteroaryl refers to a mono or bicyclic group containing at least one 5 to 11-membered aromatic ring containing 1 to 5 heteroatoms chosen from among nitrogen, oxygen and sulphur. Non-limiting examples of this include the following groups: pyridyl, pyridazinyl, pyrazinyl, pyrimidinyl, thienyl, furyl, pyrrolyle, imidazolyl, pyrazolinyl, indolyl, benzimidazolyl, oxazolyl, thiazolyl, isothiazolyl.

The "-ene" ending means that the group in question is a bivalent radical with the same definition as the base radical in terms of both the most general aspects of the invention as well as particular, advantageous and/or preferred aspects.

The term "optionally substituted" with reference to the aryl, heteroaryl and tocopheryl group means that these groups are non-substituted or substituted by one or more halogen atoms or branched or linear ($C_1$-$C_6$) alkyl group, branched or linear ($C_2$-$C_6$) alkenyl group, linear or branched ($C_2$-$C_6$) alkynyl group, branched or linear ($C_1$-$C_{16}$) alkoxy group, hydroxy linear or branched ($C_3$-$C_{18}$) trialkylsilyl group, mercapto, alkylthio, cyano, amino (optionally substituted by one or two linear or branched ($C_1$-$C_6$) alkyl groups), nitro, carboxy, formyl, alkoxycarbonyl, aminocarbonyl (optionally substituted by one or two linear or branched ($C_1$-$C_6$) alkyl group) and carbamoyl group, it being understood that the heteroaryl groups can also be substituted by an oxo group.

The term "optionally substituted" with reference to the alkyl, alkenyl, alkynyl groups means that these groups are non substituted or substituted by one or more halogen atoms or a linear or branched ($C_1$-$C_{16}$) alkoxy group, hydroxy, mercapto, alkylthio, cyano, amino (optionally substituted by one or two ($C_1$-$C_6$) alkyl group) nitro, carboxy, formyl, alkoxycarbonyl, aminocarbonyl (optionally substituted by one or two linear or branched ($C_1$-$C_6$) alkyl groups) and carbamoyl groups.

The term amino acid residue means the residues of natural α-amino acids such as Ala, Arg, Asn, Asp, Cys, Gln, Glu, Gly, His, Ile, Leu, Lys, Met, Phe, Pro, Ser, Thr, Trp, Tyr, and Val, or non-natural amino acid residues such as β-alanine, allylglycine, etc.

The term osidic residues means a radical corresponding to a sugar (or carbohydrate) derivative such as glucose, galactose, fructose, mannose, fucose, rhamnose, it being understood that in these residues, one or more hydroxy groups can be protected by a group commonly used for this purpose such as the benzyl, acetyl or benzoyl group.

The term fatty acid residue means a radical corresponding to a linear or branched fatty acid with 4 to 30 carbon atoms. This radical can originate from an essential fatty acid or a non-essential fatty acids. The following are examples of acid residues: butyric, valerianic, capronic, caprylic, capric, lauric, myristic, palmitic, stearic, arachinic, behenic, oleic, linoleic, linolenic, arachidonic, azelaic, lipoic acids.

These radicals can be non-substituted or substituted by one or more halogen atoms or a linear or branched ($C_1$-$C_{16}$) alkoxy group, a hydroxy group optionally esterified (preferably acetylated) or a mercapto, alkylthio, cyano, protected or non-protected amino (optionally substituted by one or two linear or branched $C_1$-$C_6$ alkyl groups), nitro, carboxy, formyl, alkoxycarbonyl, aminocarbonyl (optionally substituted by one or two linear or branched $C_1$-$C_6$ groups) or carbamoyl group.

The tocopheryl radical can be derived from all types of tocopherols: alpha, beta, gamma or delta.

Given the chiral nature of these residues, the anomeric carbon configuration can be an α, β or a mixture of α-β in varying proportions.

Within the scope of this invention, the preferred aryl group is the phenyl group.

The alkyl radicals in the compounds of formula (I) according to the invention are preferably linear or branched ($C_1$-$C_6$) alkyl radicals. In particular, they can be methyl, ethyl, propyl, isopropyl, butyl, sec-butyl, tert-butyl, pentyl, isopentyl, hexyl radicals.

The alkenyl radicals in compounds of formula (I) according to the invention are advantageously linear or branched ($C_2$-$C_6$) alkenyl radicals, for example allyl or vinyl groups.

Alkynyl radical in compounds of formula (I) according to the invention are advantageously linear or branched ($C_2$-$C_6$) alkynyl radicals, for example alcyn, propyn, butyn radicals.

In the compounds of formula (I), the $R_1$ group advantageously represents $R'_1$, group chosen from among —COOH, —COOR$_3$, —CHO, —CH$_2$OH, —CH$_2$OR$_5$, wherein R$_3$ and R$_5$ are as defined previously.

In accordance with another advantageous characteristic of the invention, A represents a methylene group in the compound of general formula (I).

Compounds that are well-suited to the embodiment of this invention are compounds of formula (I) wherein $R_2$ represents an —$R'_2$—O—$R_6$ group in which $R'_2$ is an arylene group, optionally substituted, and $R_6$ represents a linear or branched ($C_1$-$C_6$) alkyl group or osidic residue.

Other compounds of formula (I) which are well-suited to the embodiment of the present invention are compounds wherein $R_2$ represents a —$R'_2$—O—$R_6$ group in which $R'_2$ is phenylene and $R_6$ represents an osidic residue, preferably glucose, galactose, fructose, mannose, fucose, rhamnose.

Among the compounds of formula (I), the following compounds will be more particularly preferred:

(2E,4E,6E,8E)-3,7-dimethyl-9-{2,6,6-trimethyl-3-[4-((2S,3R,4S,5S,6R)-3,4,5-trihydroxy-6-hydroxymethyl-tetrahydro-pyran-2-yloxy)-phenoxy]-cyclohex-1-enyl}-nona-2,4,6,8-tetraenoic acid,

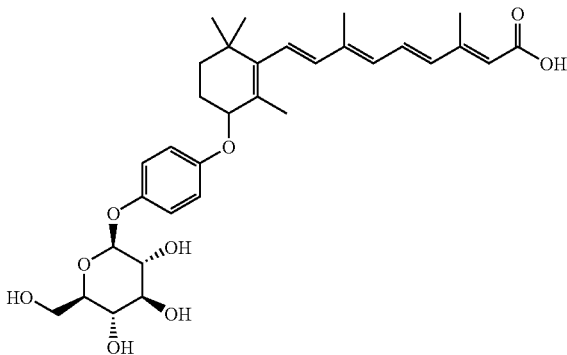 [SMILES: CC1=C(/C=C/C(C)=C/C=C/C(C)=C/C(=O)O)C(C)(C)CCC1Oc1ccc(O[C@@H]2O[C@H](CO)[C@@H](O)[C@H](O)[C@H]2O)cc1]

tert-butyl ester of (2E,4E,6E,8E)-9-[3-(4-methoxy-phenoxy)-2,6,6-trimethyl-cyclohex-1-enyl]-3,7-dimethyl-nona-2,4,6,8-tetraenoic acid,

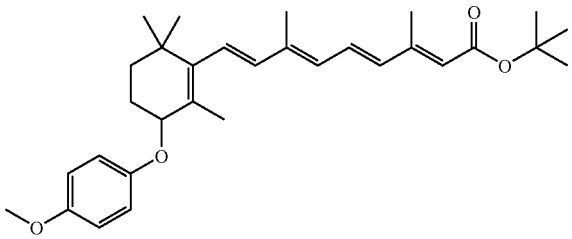 [SMILES: COc1ccc(OC2CCC(C)(C)C(/C=C/C(C)=C/C=C/C(C)=C/C(=O)OC(C)(C)C)=C2C)cc1]

(2E,4E,6E,8E)-9-[3-(4-methoxy-phenoxy)-2,6,6-trimethyl-cyclohex-1-enyl]-3,7-dimethyl-nona-2,4,6,8-tetraenal,

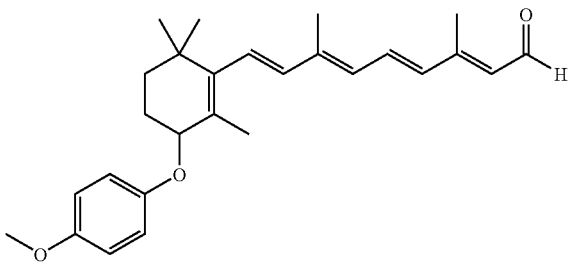 [SMILES: COc1ccc(OC2CCC(C)(C)C(/C=C/C(C)=C/C=C/C(C)=C/C=O)=C2C)cc1]

tert-butyl ester of (2E,4E,6E,8E)-9-[3-(4-hydroxy-phenoxy)-2,6,6-trimethyl-cyclohex-1-enyl]-3,7-dimethyl-nona-2,4,6,8-tetraenoic acid,

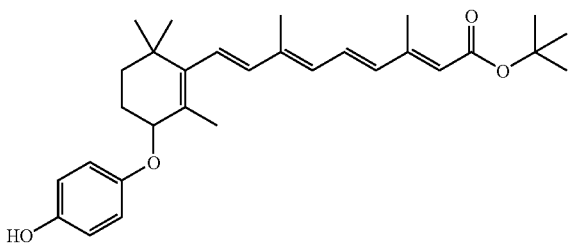 [SMILES: CC1=C(/C=C/C(C)=C/C=C/C(C)=C/C(=O)OC(C)(C)C)C(C)(C)CCC1Oc1ccc(O)cc1]

(2E,4E,6E,8E)-9-[3-(4-hydroxy-phenoxy)-2,6,6-trimethyl-cyclohex-1-enyl]-3,7-dimethyl-nona-2,4,6,8-tetraenal

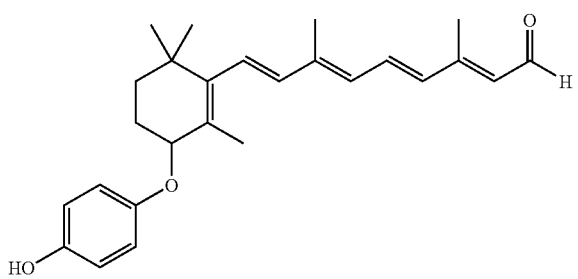 [SMILES: CC1=C(/C=C/C(C)=C/C=C/C(C)=C/C=O)C(C)(C)CCC1Oc1ccc(O)cc1]

(2E,4E,6E,8E)-3,7-dimethyl-9-{2,6,6 trimethyl-3-dimethyl-[4-((2S,3R,4S,5S,6R)-3,4,5-trihydroxy-6-hydroxymethyl-tetrahydro-pyran-2-yloxy)-phenoxy]-cyclohex-1-enyl}-nona-2,4,6,8-tetraenal,

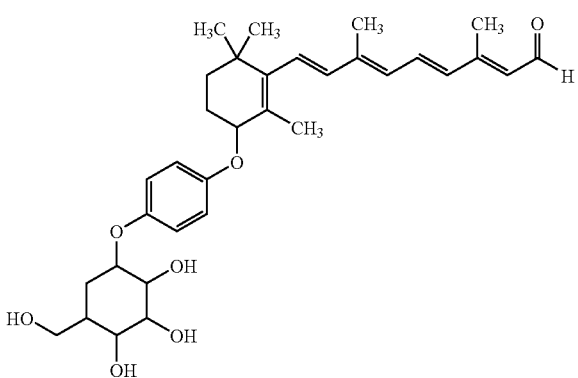 [SMILES: CC1=C(/C=C/C(C)=C/C=C/C(C)=C/C=O)C(C)(C)CCC1Oc1ccc(OC2CC(CO)C(O)C(O)C2O)cc1]

9-[(3-trans decenoate)-2,6,6 trimethyl-cyclohex-1-enyl]-3,7-dimethylnona-2,4,6,8 tetraenal,

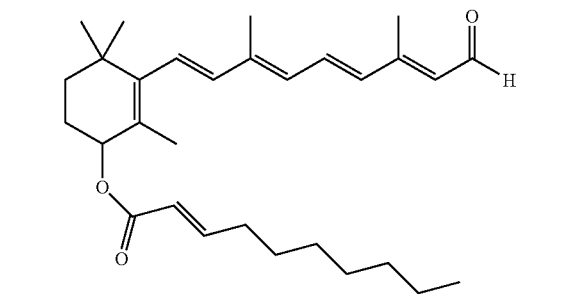 [SMILES: CCCCCCC/C=C/C(=O)OC1CCC(C)(C)C(/C=C/C(C)=C/C=C/C(C)=C/C=O)=C1C]

9-[(3-oleate)-2,6,6-trimethyl-cyclohex-1-enyl]-3,7-dimethyl-nona-2,4,6,8 tetraenal,

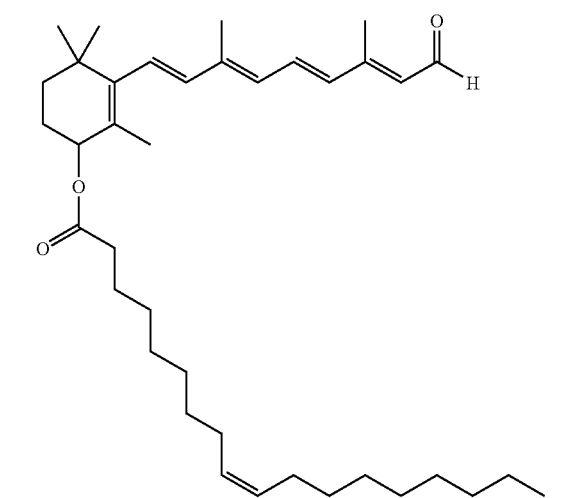 [SMILES: CCCCCCCC/C=C\CCCCCCCC(=O)OC1CCC(C)(C)C(/C=C/C(C)=C/C=C/C(C)=C/C=O)=C1C]

9-[(3-linoleate)-2,6,6-trimethyl-cyclohex-1-enyl]-3,7-dimethyl-nona-2,4,6,8-tetraenal,

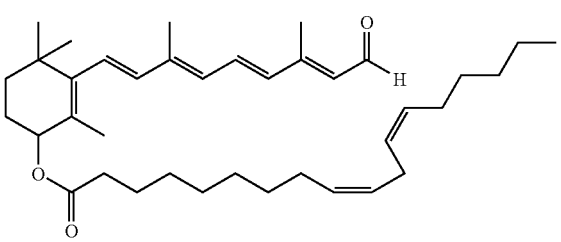 [SMILES: CCCCC/C=C\C/C=C\CCCCCCCC(=O)OC1CCC(C)(C)C(/C=C/C(C)=C/C=C/C(C)=C/C=O)=C1C]

9-[(3-linolenate)-2,6,6-trimethyl-cyclohex-1-enyl]-3,7-dimethylnona-2,4,6,8-tetraenal,

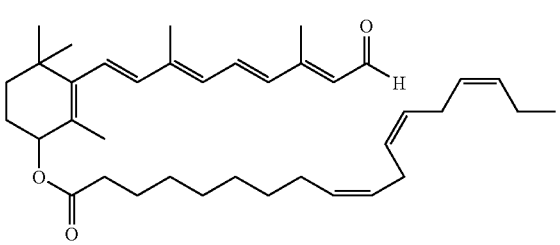 [SMILES: CC/C=C\C/C=C\C/C=C\CCCCCCCC(=O)OC1CCC(C)(C)C(/C=C/C(C)=C/C=C/C(C)=C/C=O)=C1C]

9-[(3-lipoate)-2,6,6-trimethyl-cyclohex-1-enyl]-3,7-dimethylnona-2,4,6,8-tetraenal,

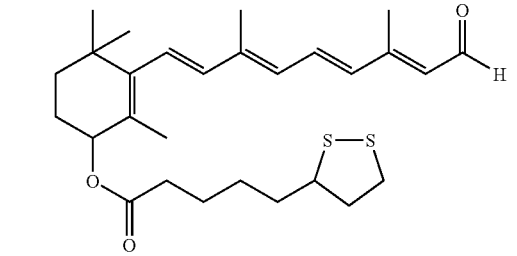 [SMILES: CC1=C(/C=C/C(C)=C/C=C/C(C)=C/C=O)C(C)(C)CCC1OC(=O)CCCCC1CCSS1]

9-[{3-(8-hydroxy-5-methyl-2-octenoate)}-2,6,6-trimethyl-cyclohex1-enyl]-3,7-dimethyl-nona-2,4,6,8-tetraenal

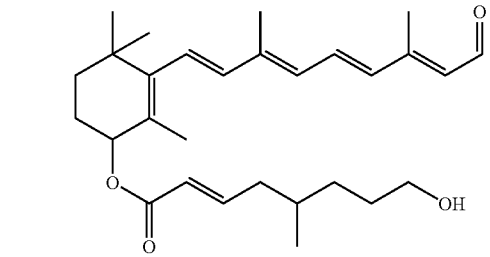 [SMILES: CC1=C(/C=C/C(C)=C/C=C/C(C)=C/C=O)C(C)(C)CCC1OC(=O)/C=C/CC(C)CCCO]

3-((1E,3E,5E,7E)-3,7-dimethyl-9-oxo-nona-1,3,5,7-tetraenyl)-2,4,4-trimethyl-cyclohex-2-enyl ester of (E)-14-Hydroxy-tetradec-2-enoic acid

7

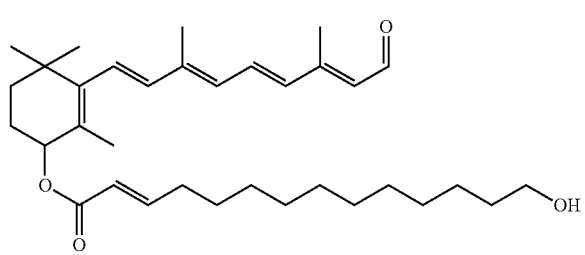 [SMILES: CC1=C(/C=C/C(C)=C/C=C/C(C)=C/C=O)C(C)(C)CCC1OC(=O)/C=C/CCCCCCCCCCCO]

3-((1E,3E,5E,7E)-3,7-dimethyl-9-oxo-nona-1,3,5,7-tetraenyl)-2,4,4-trimethyl-cyclohex-2-enyl ester of (E)-10-Hydroxy-dec-2-enoic acid

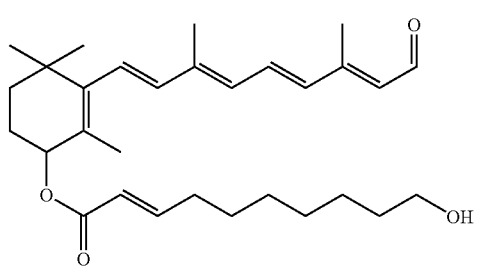 [SMILES: CC1=C(/C=C/C(C)=C/C=C/C(C)=C/C=O)C(C)(C)CCC1OC(=O)/C=C/CCCCCCCO]

3-((1E,3E,5E,7E)-3,7-dimethyl-9-oxo-nona-1,3,5,7-tetraenyl)-2,4,4-trimethyl-cyclohex-2-enyl ester of (E)-10-Acetoxy-dec-2-enoic acid

8

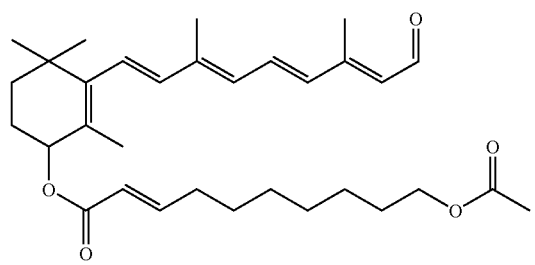 [SMILES: CC(=O)OCCCCCCC/C=C/C(=O)OC1CCC(C)(C)C(/C=C/C(C)=C/C=C/C(C)=C/C=O)=C1C]

9-[(3-tetraacetyl glucose)-2,6,6-trimethyl-cyclohex-1-enyl]-3,7-dimethylnona-2,4,6,8-tetraenal 3-((1E,3E,5E,7E)-3,7-dimethyl-9-oxo-nona-1,3,5,7-tetraenyl)-2,4,4-trimethyl-cyclohex-2-enyl and (R)-2,8-dimethyl-2-((4R,8R)-4,8,12-trimethyltridecyl)-1-benzopyran-6-yl bis ester of heptane dioic acid

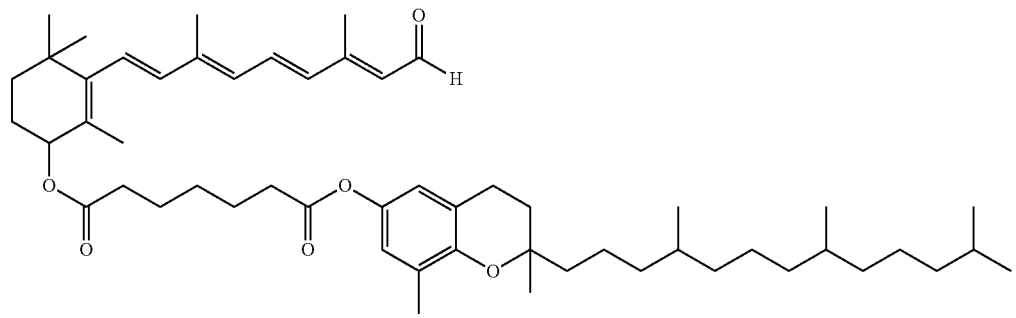 [SMILES: CC1=C(/C=C/C(C)=C/C=C/C(C)=C/C=O)C(C)(C)CCC1OC(=O)CCCCCC(=O)Oc1cc(C)c2c(c1)CCC(C)(CCCC(C)CCCC(C)CCCC(C)C)O2]

3-((1E,3E,5E,7E)-3,7-dimethyl-9-oxo-nona-1,3,5,7-tetraenyl)-2,4,4-trimethyl-cyclohex-2-enyl and (R)-2,8-dimethyl-2-((4R,8R)-4,8,12-trimethyltridecyl)-1-benzopyran-6-yl bis ester of nonanedioic acid

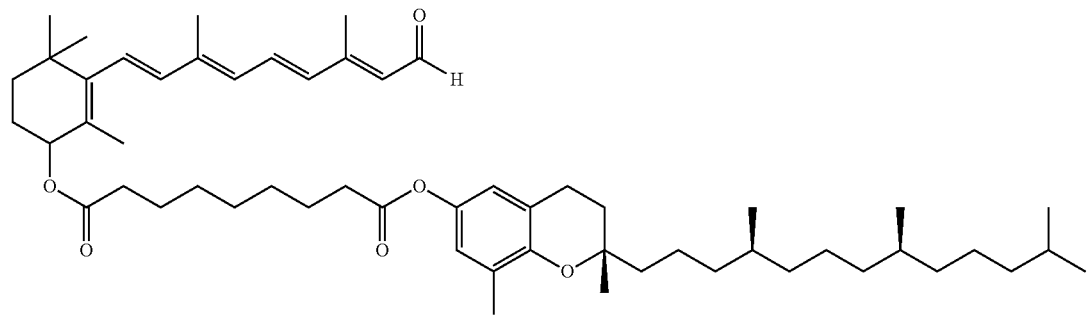 [SMILES: CC1=C(/C=C/C(C)=C/C=C/C(C)=C/C=O)C(C)(C)CCC1OC(=O)CCCCCCCC(=O)Oc1cc(C)c2c(c1)CC[C@](C)(CCC[C@@H](C)CCC[C@@H](C)CCCC(C)C)O2]

3-((1E,3E,5E,7E)-3,7-dimethyl-9-oxo-nona-1,3,5,7-tetraenyl)-2,4,4-trimethyl-cyclohex-2-enyl and (R)-2,8-dimethyl-2-((4R,8R)-4,8,12-trimethyltridecyl)-1-benzopyran-6-yl bis ester of succinic acid

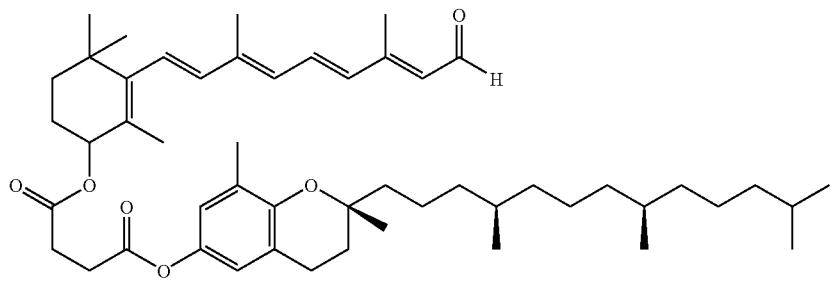 [SMILES: CC1=C(/C=C/C(C)=C/C=C/C(C)=C/C=O)C(C)(C)CCC1OC(=O)CCC(=O)Oc1cc(C)c2c(c1)CC[C@@](C)(CCC[C@H](C)CCC[C@H](C)CCCC(C)C)O2]

3-((1E,3E,5E,7E)-3,7-dimethyl-9-oxo-nona-1,3,5,7-tetraenyl)-2,4,4-trimethyl-cyclohex-2-enyl and (R)-2,8-dimethyl-2-((4R,8R)-4,8,12-trimethyltridecyl)-1-benzopyran-6-yl bis ester of pentanedioic acid

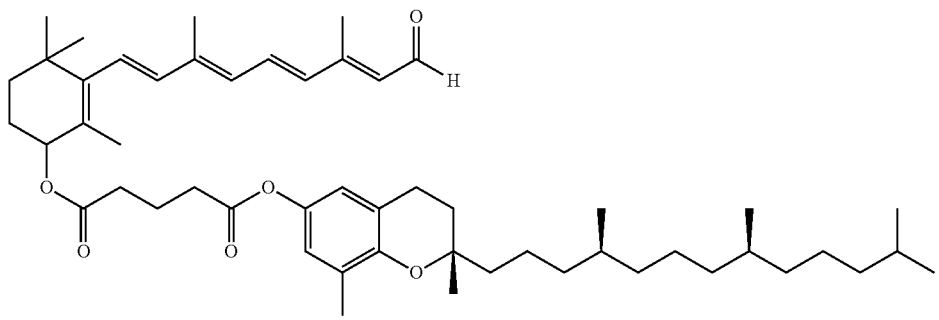 [SMILES: CC1=C(/C=C/C(C)=C/C=C/C(C)=C/C=O)C(C)(C)CCC1OC(=O)CCCC(=O)Oc1cc(C)c2c(c1)CC[C@](C)(CCC[C@@H](C)CCC[C@@H](C)CCCC(C)C)O2]

This invention also relates a method for preparing compounds of formula (I) wherein the compound of formula (II):

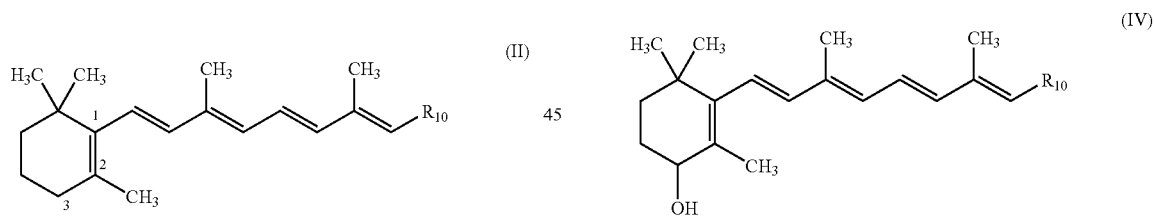

wherein $R_{10}$ has the same meaning as the $R_1$ radical defined previously, with the exception of the —$CH_2OH$ group, and undergoes an allylic oxidation reaction in position 3 to yield a compound of formula (III):

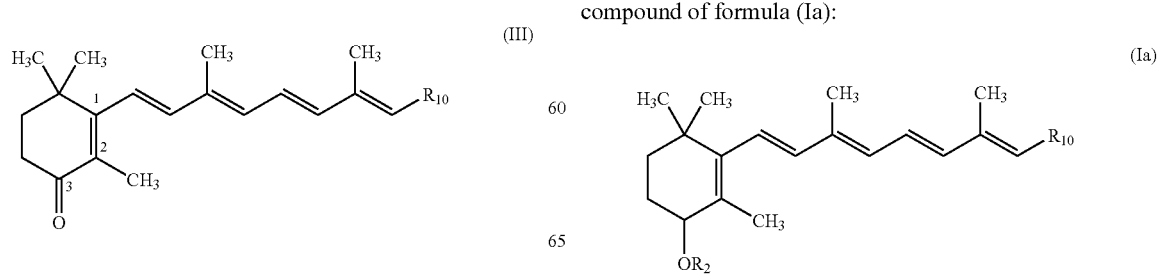

wherein $R_{10}$ is as defined previously, whose carbonyl group in position 3 is then reduced to the corresponding alcohol of formula (IV):

(IV)

compound (IV) undergoes an alkylation reaction or coupling reaction in alkaline, acid or neutral medium, possibly in the presence of a coupling reagent, using a reagent of formula $R_2$—X wherein X represents a hydroxy group or a halogen atom, it being understood that the hydroxy group can be activated in the form of a starting group, if need be, to yield a compound of formula (Ia):

(Ia)

particular case of compounds of formula (I) wherein $R_2$ is as defined previously and $R_{10}$ has the same meaning as above, which, when the $R_{10}$ radical represents a —$COOR_3$ group, can undergo a hydrolysis or reduction reaction to yield a compound of formula (Ib):

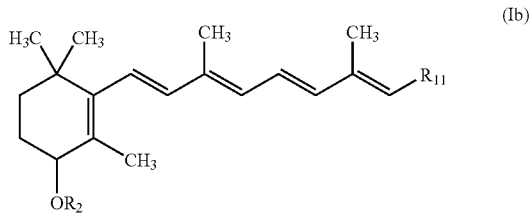

(Ib)

particular case of compounds of formula (I) wherein $R_2$ is as defined previously and $R_{11}$ represents a —COOH or $CH_2OH$ group, it being understood that the different groups present in the preceding compounds are suitable for the synthesis of protected then deprotected groups at any time, depending on their incompatibility with the reagents used. Protective groups that can be used within the scope of this invention are chosen from among commonly used groups such as those described in <<Protective Group in Organic Synthesis, Wiley-Interscience, 3rd Edition, 1999>>.

The oxidation reaction in position 3 of the compound of formula (II) is carried out using conventional oxidants for allylic positions, which include selenium oxide, sodium hypochlorite, ruthenium oxide, chromium oxide and manganese oxide. Preferably, manganese oxide is used. The reaction can be carried out in a variety of solvents such as dichloromethane, dichloro-1,2-ethane, tetrahydrofuran, pentane or hexane. The temperature in the reaction medium can be a low temperature, room temperature or under reflux depending on the solvent chosen.

Reduction of the carbonyl group of the compound of formula (III) is preferably carried out using hydrides, such as aluminium or boron hydrides, and more particularly blocked and de-activated aluminium hydride at a low temperature. Advantageously diisobutylaluminium hydride (DIBAL-H) is chosen under temperature conditions ranging from −20° C. to −70° C. in an ether-containing solvent such as tetrahydrofuran or dioxane but also in toluene.

The alkylation reaction of the compound of formula (IV) giving rise to compounds of formula (Ia) or (Ib) will, for example, be a Mitsunobu reaction wherein the alkylation agent is a phenol activated by a combination of phosphene and diaxocarboxylate, more specifically triphenylphosphine and diisopropyl diisocarboxylate (DIAD).

Hydrolysis or the optional reduction of the $R_{10}$ group present in compounds of formula (Ia) can be carried out using conventional reagents such as tetrabutylammonium fluoride for hydrolysis and DIBAL-H for reduction.

The invention also relates compounds of formula (IIIa):

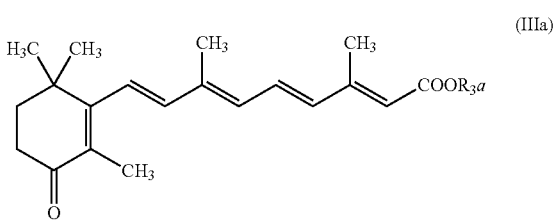

(IIIa)

wherein the $R_3$a group represents a branched $C_3$-$C_{16}$ alkyl group. This compound is mentioned above and is used as a synthesis intermediate to obtain certain compounds of formula (I).

The invention also relates compounds of formula (IVa):

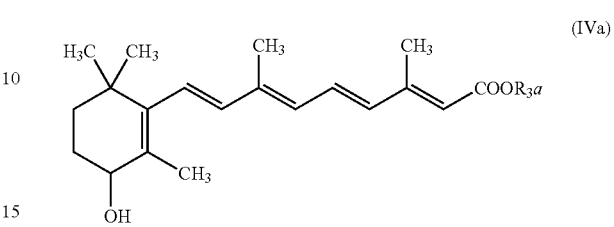

(IVa)

wherein $R_3$a represents a branched $C_3$-$C_{16}$ alkyl group, a compound mentioned previously and used within the scope of this invention as a synthesis intermediate to obtain a number of compounds of formula (I).

In an advantageous aspect, in the compounds of formula (IIIa) and (IVa) the $R_{3a}$ group represents a tert-butyl group.

Among these compounds (IIIa, IVa), the following can be mentioned in particular:

tert-butyl ester of (2E,4E,6E,8E)-3,7-dimethyl-9-(2,6,6-trimethyl-3-oxo-cyclohex-1-enyl)-nona-2,4,6,8-tetranoic acid,

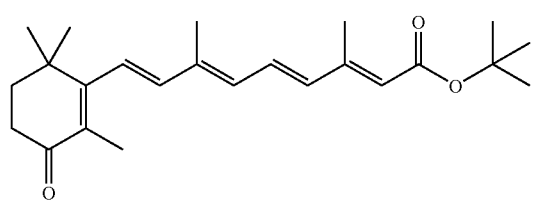 [SMILES: CC1=C(/C=C/C(C)=C/C=C/C(C)=C/C(=O)OC(C)(C)C)C(C)(C)CCC1=O]

tert-butyl ester of (2E,4E,6E,8E)-9-(3-Hydroxy-2,6,6-trimethyl-cyclohex-1-enyl)-3,7-dimethyl-nona-2,4,6,8-tetranoic acid.

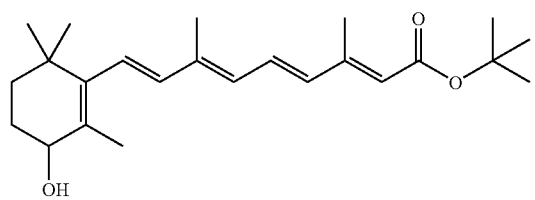 [SMILES: CC1=C(/C=C/C(C)=C/C=C/C(C)=C/C(=O)OC(C)(C)C)C(C)(C)CCC1O]

The compounds of formula (I) as defined above have shown a good ability to inhibit the production of melanin by melanocytes, thus demonstrating their benefits in the cosmetic and/or dermatological field. This invention therefore concerns a composition wherein it contains at least one compound of formula (I) as defined above in a physiologically acceptable medium.

The composition of the invention is particularly intended for topical application. In addition, it includes a physiologically acceptable medium, in other words a medium that is compatible with the skin, including the scalp, mucous membranes, head hair, body hair and/or eyes and can constitute a cosmetic and dermatological composition.

The derivatives of the invention, alone or in combination, as well as the composition containing them, can be used topically for application to the skin, body hair and/or head hair.

The amount of derivatives that can be used within the scope of the invention evidently depends on the desired effect.

As an example, this amount can range from 0.01% to 5% by weight, preferably 0.05% to 0.5% by weight, with respect to the total weight of the composition.

The compounds of formula (I) have the advantage of having extremely low toxicity and have shown good inhibitory properties of the production of melanin by the melanocytes. Moreover, they have fewer side effects (skin dryness and inflammation) than standard products currently in use, for example retinoic acid or other synthetic acids of the same type. They also have better stability.

Another aspect of the invention relates a cosmetic method for whitening and/or lightening the skin and/or body hair and/or head hair, including application to the skin and/or body hair and/or head hair of a cosmetic composition containing at least one compound of formula (I) as defined previously.

The invention also relates a cosmetic method for removing brown pigment patches and/or age spots from human skin, including application to the skin of a cosmetic composition containing at least one compound of formula (I) as defined previously.

In one variant, the invention relates the use of at least one compound of formula (I) as a medication.

More particularly, the invention relates the use of at least one compound of formula (I) as defined previously for the manufacture of a dermatological composition intended for use in depigmenting skin and/or body hair and/or head hair.

The invention also relates pharmaceutical compositions containing at least one compound of formula (I) as defined previously, alone or in combination with one or more pharmaceutically acceptable excipients.

Among the pharmaceutical compositions according to the invention, we may mention in particular those suited to oral, parenteral, nasal, per- or transcutaneous, rectal, perlingual, ocular or respiratory administration, and for example tablets or coated pills, sublingual tablets, sachets, capsules, gel capsules, suppositories and injectable or drinkable vials.

The following examples illustrate the invention without limiting its scope. The compounds are, depending on the case, given either with their chemical names or their CTFA names (International Cosmetic Ingredient Dictionary and Handbook).

Preparation A

Step 1: Peracetylated Arbutin

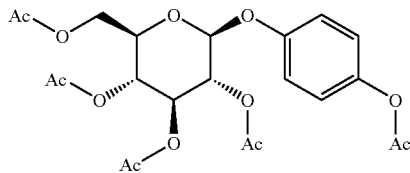 [SMILES: CC(=O)OC[C@H]1O[C@@H](Oc2ccc(OC(C)=O)cc2)[C@H](OC(C)=O)[C@@H](OC(C)=O)[C@@H]1OC(C)=O]

15 g (55.1 mmol) of Arbutin was dissolved in 7 volumes of pyridine, then 55 ml (0.5 mol) of acetic anhydride was added. The reaction medium was stirred for 18 h. After concentration to half the volume, the medium was poured slowly into 100 volumes of distilled water with vigorous stirring. The resulting white solid was filtered, washed in water and dried under vacuum at 30° C. to yield 25.9 g (53.7 mmol) of a white solid.

Rf=0.4 (toluene/ethyl acetate 1/1)

Step 2: tetra-acetylated Arbutin

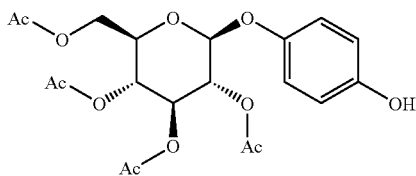 [SMILES: CC(=O)OC[C@H]1O[C@@H](Oc2ccc(O)cc2)[C@H](OC(C)=O)[C@@H](OC(C)=O)[C@@H]1OC(C)=O]

25.9 g (53.7 mmol) of peracetylated Arbutin was dissolved in 10 volumes of methanol and 10 volumes of tetrahydrofuran, under nitrogen flux and out of direct light. A spatula-tip amount of potassium carbonate was added and the medium was stirred for 1 h30. Thin layer chromatography was used to stop the reaction before total deacetylation takes place. After hydrolysis in 2 volumes of 1M HCl, the medium was extracted by dichloromethane. The organic phases were washed in a saturated NaCl solution, dried on $MgSO_4$, filtered and concentrated under vacuum to yield 18 g (40.9 mmol) of a white solid.

Rf=0.6 (toluene/ethyl acetate 1/1)

EXAMPLE 1

2-trimethylsilanyl-ethyl ester of (2E,4E,6E,8E)-3,7-dimethyl-9-[{2,6,6-trimethyl-3-(4-((2S,3R,4S,5R,6R)-3,4,5-triacetoxy-6-acetoxymethyltetrahydropyran-2-yloxy)-phenoxy]cyclohex-1-enyl}-nona-2,4,6,8-tetranoic acid Step 1

2-trimethylsilanyl-ethyl ester of (2E,4E,6E,8E)-3,7-dimethyl-9-(2,6,6-trimethyl-cyclohex-1-enyl)-nona-2,4,6,8-tetranoic acid

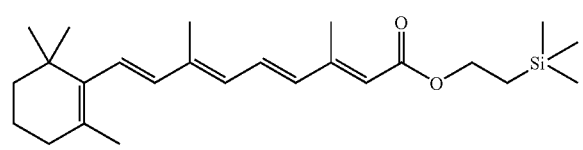 [SMILES: CC1=C(/C=C/C(C)=C/C=C/C(C)=C/C(=O)OCC[Si](C)(C)C)C(C)(C)CCC1]

40 g (0.13 mol) of retinoic acid was dissolved in 65 volumes of ethyl acetate under nitrogen flux and out of direct light. 27.5 g (0.13 mol) of dicyclohexylcarbodiimide, 19.3 ml (0.136 mol) of trimethylsilylethanol and 6.3 g (0.05 mol) of dimethylaminopyridine were added at 0° C. The reaction medium was stirred at room temperature for 18 h. After filtration on celite, the filtrate was concentrated under vacuum. 30 g of the crude product were purified on a silica column and eluted with toluene to yield 22 g (0.055 mol) of a yellow solid.

Rf=0.8 (heptane/ethyl acetate 8/2)

Step 2

2-trimethylsilanyl-ethyl ester of (2E,4E,6E,8E)-3,7-dimethyl-9-(2,6,6-trimethyl-3-oxo-cyclohex-1-enyl)-nona-2,4,6,8-tetranoic acid

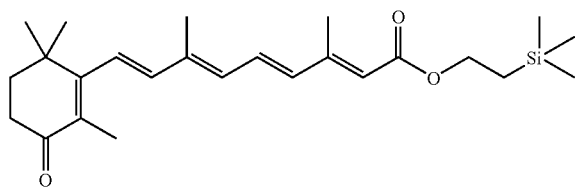 [SMILES: CC1=C(/C=C/C(C)=C/C=C/C(C)=C/C(=O)OCC[Si](C)(C)C)C(C)(C)CCC1=O]

22 g (55.0 mmol) of the compound described in step 1 was dissolved in 40 volumes of dichloromethane under nitrogen flux and out of direct light. 329 g (3.78 mol) of manganese oxide was added and the mixture was stirred for 24 h. The medium was filtered on celite and concentrated under vacuum. 25 g of the crude product were purified on a silica column and eluted on a heptane/ethyl acetate gradient to yield 14.3 g (34.5 mmol) of an orange solid.

Rf=0.5 (heptane/ethyl acetate 7/3)

Step 3

2-trimethylsilanyl-ethyl ester of (2E,4E,6E,8E)-9-(3-Hydroxy-2,6,6-trimethyl-cyclohex-1-enyl)-3,7-dimethyl-nona-2,4,6,8-tetranoic acid

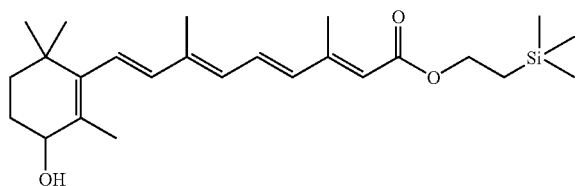 [SMILES: CC1=C(/C=C/C(C)=C/C=C/C(C)=C/C(=O)OCC[Si](C)(C)C)C(C)(C)CCC1O]

14.3 g (34.5 mmol) of the compound described in step 2 was dissolved in 10 volumes of tetrahydrofuran under nitrogen flux and out of direct light. The medium was cooled to −78° C. and 29 ml (35.2 mmol) of a 20% Dibal-H solution in toluene was added drop by drop, with the temperature maintained at −78° C. The medium was stirred for 5 h. 20 volumes of a saturated solution of Rozen salts was added slowly −78° C. The medium was extracted by means of ethyl acetate. The organic phases were washed in a saturated NaCl solution, dried on MgSO4 and concentrated under vacuum. 16 g of the crude product were purified on a silica column and eluted on a heptane/ethyl acetate gradient to yield 10 g (24.0 mmol) of a yellow solid.

Rf=0.4 (heptane/ethyl acetate 7/3)

Step 4

2-trimethylsilanyl-ethyl ester of (2E,4E,6E,8E)-3,7-dimethyl-9-{2,6,6-trimethyl-3-[4-((2S,3R,4S,5R,6R)-3,4,5-triacetoxy-6-acetoxymethyltetrahydro-pyran-2-yloxy)-phenoxy]cyclohex-1-enyl}-nona-2,4,6,8-tetraenoic acid

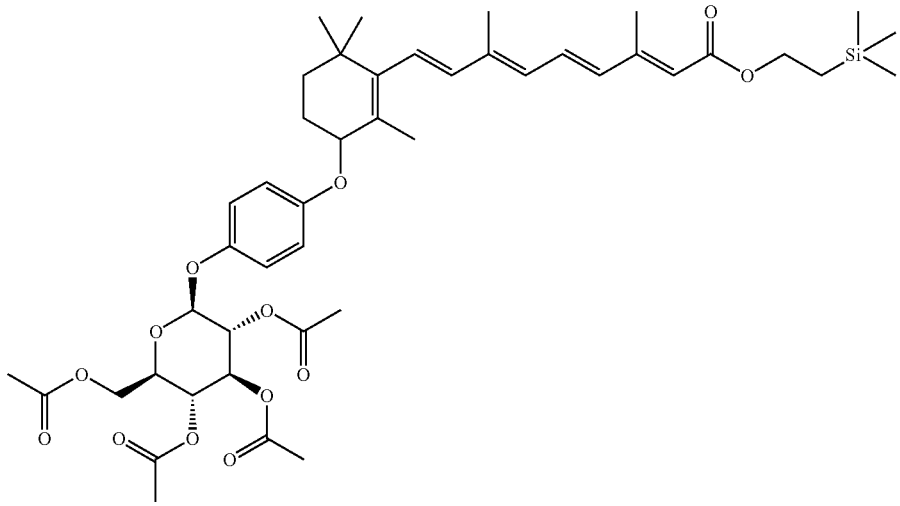 [SMILES: CC(=O)OC[C@H]1O[C@@H](Oc2ccc(OC3CCC(C)(C)C(/C=C/C(C)=C/C=C/C(C)=C/C(=O)OCC[Si](C)(C)C)=C3C)cc2)[C@H](OC(C)=O)[C@@H](OC(C)=O)[C@@H]1OC(C)=O]

11.8 g (26.8 mmol) of tetra-acetylated arbutin (see preparation A) was dissolved in 10 volumes of tetrahydrofuran and 3 volumes of toluene under nitrogen flux. A freshly prepared solution of 5.2 ml (29.5 mmol) of diisopropyl azodicarboxylate with 10.4 g (40.2 mmol) of triphenylphosphine in 10 volumes of toluene was added drop by drop at −5° C. The medium was stirred at 0° C. for 10 minutes then 5 g (12.0 mmol) of the compound described in step 3 in 10 volumes of toluene was added slowly. The mixture was stirred for 20 h. The medium was concentrated under vacuum and the residue was purified on a silica column and eluted on a heptane/ethyl acetate gradient to yield 3.0 g (3.6 mmol) of a yellow solid.

Rf=0.3 (heptane/ethyl acetate 7/3)

Mass spectrometry: [MNa+] 861 (calculated [MH+] 839)

EXAMPLE 2

2-trimethylsilanyl-ethyl ester of (2E,4E,6E,8E)-3,7-dimethyl-9-{2,6,6-trimethyl-3-[4-((2S,3R,4S,5S,6R)-3,4,5-trihydroxy-6-hydroxymethyltetrahydro-pyran-2-yloxy)-phenoxy]-cyclohex-1-enyl}-nona-2,4,6,8-tetraenoic acid

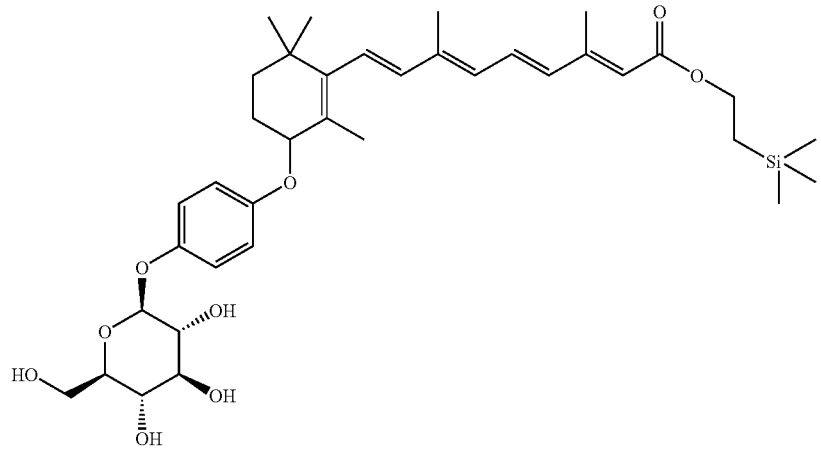 [SMILES: CC1=C(/C=C/C(C)=C/C=C/C(C)=C/C(=O)OCC[Si](C)(C)C)C(C)(C)CCC1Oc1ccc(O[C@@H]2O[C@H](CO)[C@@H](O)[C@H](O)[C@H]2O)cc1]

0.5 g (0.6 mmol) of the compound of example 1 was dissolved, out of direct light, in 4 volumes of tetrahydrofuran. 3 volumes of methanol were then added as well as a spatula-tip of potassium carbonate. The mixture was stirred for 6 h. After hydrolysis in distilled water, the medium was concentrated and extracted with dichloromethane. The organic phases were washed in a saturated NaCl solution, dried on $MgSO_4$ and concentrated under vacuum to yield 30 g (0.04 mmol) of a pale yellow solid.

Rf=0.1 (heptane/ethyl acetate 7/3)

Mass spectrometry: [MNa+] 693 (calculated [MH+] 671)

EXAMPLE 3

(2E,4E,6E,8E)-3,7-dimethyl-9-{2,6,6-trimethyl-3-[4-((2S,3R,4S,5S,6R)-3,4,5-trihydroxy-6-hydroxymethyl-tetrahydro-pyran-2-yloxy)-phenoxy]-cyclohex-1-enyl}-nona-2,4,6,8-tetraenoic acid

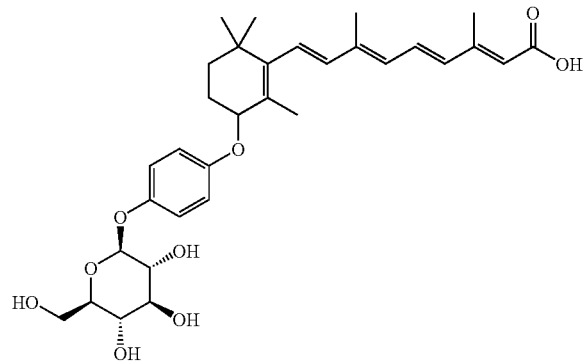 [SMILES: CC1=C(/C=C/C(C)=C/C=C/C(C)=C/C(=O)O)C(C)(C)CCC1Oc1ccc(O[C@@H]2O[C@H](CO)[C@@H](O)[C@H](O)[C@H]2O)cc1]

0.5 g (0.6 mmol) of the compound of example 1 was placed in suspension in 10 volumes of ethanol, out of direct light. 0.3 ml (0.6 mmol) of a 2M soda solution was added to the reaction medium. The mixture was stirred for 7 h. 1.8 ml of 2M soda was added again. After acid hydrolysis (6N HCl) to pH=5.8, the medium was filtered and the solid residue dried under vacuum to yield 0.07 g (0.12 mmol) of a pale yellow solid.

Rf=0.1 dichloromethane/methanol 9/1)

Mass spectrometry: [MNa+] 593 (calculated [MH+] 571)

EXAMPLE 4

Tert-butyl ester of (2E,4E,6E,8E)-9-[3-(4-Methoxy-phenoxy)-2,6,6-trimethyl-cyclohex-1-enyl]-3,7-dimethyl-nona-2,4,6,8-tetraenoic acid Step 1

Tert-butyl ester of (2E,4E,6E,8E)-3,7-dimethyl-9-(2,6,6-trimethylcyclohex-1-enyl)-nona-2,4,6,8-tetraenoic acid

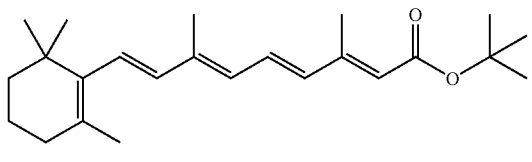 [SMILES: CC1=C(/C=C/C(C)=C/C=C/C(C)=C/C(=O)OC(C)(C)C)C(C)(C)CCC1]

9.1 g (30.3 mmol) of retinoic acid was dissolved in 10 volumes of dichloromethane. 14 g (69.6 mmol) of 2-tert-butyl-1,3-diisopropyl-isourea was added at room temperature under nitrogen flux and out of direct light. The medium was stirred for 18 h. Thin layer chromatography screening showed the reaction endpoint (UV detection). The urea salts were then filtered. The filtrate was concentrated out of direct light and purified on a silica column with heptane/ethyl acetate 9/1 out of direct light as the eluent to yield 10.4 g (29.2 mmol) of a creamy oil.

Rf=0.4 (heptane/ethyl acetate 8/2)

Step 2

Tert-butyl ester of (2E,4E,6E,8E)-3,7-dimethyl-9-(2,6,6-trimethyl-3-oxo-cyclohex-1-enyl)-nona-2,4,6,8-tetraenoic acid

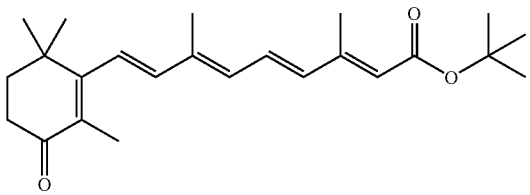 [SMILES: CC1=C(/C=C/C(C)=C/C=C/C(C)=C/C(=O)OC(C)(C)C)C(C)(C)CCC1=O]

10.4 g (29.2 mmol) of the compound of step 1 was dissolved in 40 volumes of dichloromethane under nitrogen flux and out of direct light. 114 g (131 mmol) of manganese oxide was added and the mixture was stirred for 72 h. The medium was filtered on celite, concentrated under vacuum and purified on a silica column using a heptane/ethyl acetate 9/1 mixture. After crystallisation, 10 g (27.0 mmol) of an orange solid was obtained.
Rf=0.5 (heptane/ethyl acetate 7/3)
Step 3

Tert-butyl ester of (2E,4E,6E,8E)-9-(3-Hydroxy-2,6,6-trimethylcyclohex-1-enyl)-3,7-dimethyl-nona-2,4,6,8-tetraenoic acid

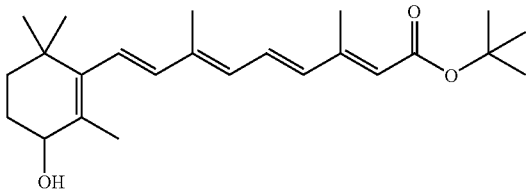 [SMILES: CC1=C(/C=C/C(C)=C/C=C/C(C)=C/C(=O)OC(C)(C)C)C(C)(C)CCC1O]

10 g (27.0 mmol) of the compound of step 2 was dissolved in 10 volumes of tetrahyrdofuran under nitrogen flux and out of direct light. The medium was cooled to −78° C. and 23 ml (27.5 mmol) of a 20% Dibal-H solution in toluene was added drop by drop, maintaining the temperature at −78° C. The medium was stirred for 3 h. 20 volumes of a saturated solution of Rozen salts was added at −60° C. The medium was extracted with dichloromethane. The organic phases were washed in a saturated NaCl solution, dried on MgSO$_4$ and concentrated under vacuum. 50 g of the crude product were purified on a silica column and eluted on a heptane/ethyl acetate gradient to yield 6.8 g (18.3 mmol) of a yellow creamy oil.
Rf=0.3 (heptane/ethyl acetate 7/3)
Step 4

Tert-butyl ester of (2E,4E,6E,8E)-9-[3-(4-Methoxy-phenoxy)-2,6,6-trimethyl-cyclohex-1-enyl]-3,7-dimethyl-nona-2,4,6,8-tetraenoic acid

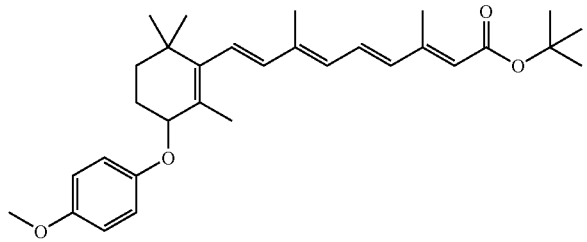 [SMILES: COc1ccc(OC2CCC(C)(C)C(/C=C/C(C)=C/C=C/C(C)=C/C(=O)OC(C)(C)C)=C2C)cc1]

0.67 g (5.2 mmol) of 4-Methoxyphenol was dissolved in 20 volumes of toluene under nitrogen flux. A freshly prepared solution of 0.58 ml (28.6 mmol) diisopropyl azodicarboxylate with 1.1 g (38.9 mmol) of triphenylphosphine in 40 volumes of toluene was added drop by drop at −5° C. The medium was stirred at 0° C. for 10 minutes. 0.97 g (26.0 mmol) of the compound of step 3 in 20 volumes of toluene was added slowly, out of direct light. The mixture was stirred for 20 h. The medium was concentrated under vacuum and the residue purified on a silica column and eluted with a heptane/ethyl acetate 98/2 system to yield 0.5 g of a yellow oil.
Rf=0.7 (heptane/ethyl acetate 8/2)
Mass spectrometry: [MNa$^+$] 501 (calculated [MH+] 479)

EXAMPLE 5

(2E,4E,6E,8E)-9-[3-(4-Methoxy-phenoxy)-2,6,6-trimethyl-cyclohex-1-enyl]-3,7-dimethyl-nona-2,4,6,8-tetraenal

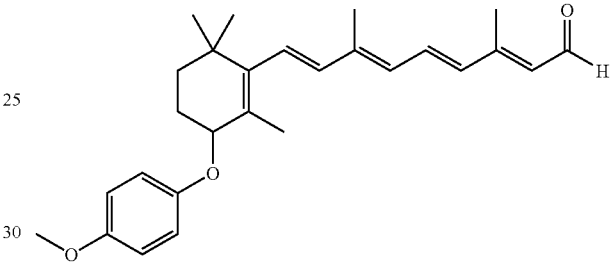

0.5 g (1.04 mmol) of the compound of example 4 was dissolved in 10 volumes of toluene under nitrogen flux and out of direct light. The medium was cooled to −78° C. and 0.89 ml (1.07 mmol) of a 20% Dibal-H solution in toluene was added drop by drop, maintaining temperature at −78° C. The medium was stirred for 10 minutes. 10 volumes of a saturated solution of Rozen salts was added at −78° C. The medium was extracted with toluene. The organic phases were washed in a saturated NaCl solution, dried on MgSO$_4$ and concentrated under vacuum. 0.8 g of the crude product was purified on a silica column and eluted on a heptane/ethyl acetate gradient. The yellow crystals obtained were washed in pentane to yield 150 mg (0.37 mmol) of a yellow solid.
Rf=0.2 (heptane/ethyl acetate 8/2)
Mass spectrometry: [MNa$^+$] 429 (calculated [MH+] 407)

EXAMPLE 6

Tert-butyl ester of (2E,4E,6E,8E)-9-[3-(4-Hydroxy-phenoxy)-2,6,6-trimethyl-cyclohex-1-enyl]-3,7-dimethyl-nona-2,4,6,8-tetraenoic acid

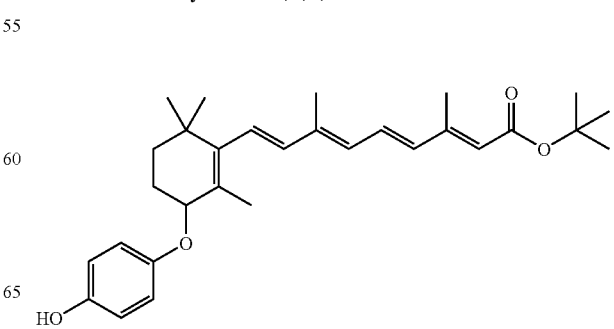

1.1 g (10.06 mmol) of hydroquinone was dissolved in 40 volumes of tetrahydrofuran under nitrogen flux. A freshly prepared solution of 0.87 ml (4.42 mmol) of diisopropyl azodicarboxylate with 1.6 g (6.04 mmol) of triphenylphosphine in 30 volumes of toluene and 30 volumes of tetrahydrofuran was added drop by drop at −5° C. The medium was stirred at 0° C. for 10 minutes then 1.5 g (4.03 mmol) of the compound of example 4 in 20 volumes of toluene was added slowly, out of direct light. The mixture was then stirred for 20 h. The medium was concentrated under vacuum and the residue was purified on a silica column and eluted in a heptane/ethyl acetate 8/2 system to yield 0.6 g of a yellow solid.

Rf=0.6 (heptane/ethyl acetate 7/3)

Mass spectrometry: [MNa+] 487 (calculated [MH+] 465)

EXAMPLE 7

(2E,4E,6E,8E)-9-[3-(4-Hydroxy-phenoxy)-2,6,6-trimethyl-cyclohex-1-enyl]-3,7-dimethyl-nona-2,4,6,8-tetraenal

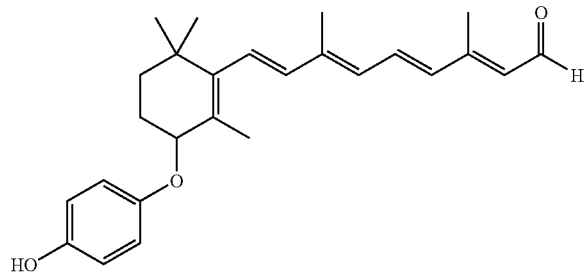 [SMILES: CC1=C(/C=C/C(C)=C/C=C/C(C)=C/C=O)C(C)(C)CCC1Oc1ccc(O)cc1]

6.9 g (31.0 mmol) of hydroquinone mono-protected by a tert-butyldimethylsilyl group was dissolved in 10 volumes of toluene under nitrogen flux. A freshly prepared solution of 7.9 ml (40.3 mmol) of diisopropyl azodicarboxylate with 12.2 g (46.5 mmol) of triphenylphosphine in 10 volumes of toluene was added drop by drop at −5° C. The medium was stirred at 0° C. for 10 minutes then 6 g (2.68 mmol) of tert-butyl ester of (2E,4E,6E,8E)-9-(3-Hydroxy-2,6,6-trimethyl-cyclohex-1-enyl)-3,7-dimethyl-nona-2,4,6,8-tetraenoic acid as obtained in step 3 of example 4 in 10 volumes of toluene was added slowly, out of direct light. The mixture was stirred for 20 h. The mixture was concentrated under vacuum and the residue was purified on a silica column and eluted on a heptane/isopropyl ether gradient. 5.16 g (8.91 mmol) of a yellow solid was obtained (55%).

Deprotection and Production of the Aldehyde Function:

1.32 g (2.28 mmol) of the previous compound was placed in solution in 10 volumes of toluene under nitrogen flux and out of direct light. The medium was cooled to −80° C. and 2.46 ml of a 20% Dibal-H solution in toluene was added slowly. The medium was stirred for 20 minutes then 20 volumes of a saturated solution of Rozen salts was added at −78° C. After vigorous stirring, the medium was extracted with toluene. The organic phases were washed in a saturated NaCl solution, dried on MgSO4 and concentrated under vacuum. The crude mixture was purified on a silica column, processed and eluted on a heptane/isopropyl ether gradient. 0.58 g (1.18 mmol) of a yellow solid was obtained (51% yield).

1.87 g (3.69 mmol) of the previous derivative was placed in solution in 10 volumes of tetrahydrofuran out of direct light. 5.2 ml (5.17 mmol) of a 1M tetrabutylammonium fluoride solution was added drop by drop at 0° C. The medium was stirred for 20 minutes then poured onto a saturated NH4Cl solution. After extraction in isopropyl ether, the organic phases were washed in a saturated NaCl solution, dried on Na2SO4 and concentrated under vacuum. The crude mixture was purified on a silica column, processed in heptane and eluted on a heptane/ethyl acetate gradient. 1 g (2.55 mmol) of an orange-red solid was obtained (69% yield.

EXAMPLE 8

9-[(3-trans decenoate)-2,6,6 trimethyl-cyclohex-1-enyl]-3,7-dimethylnona-2,4,6,8 tetraenal Step 1

9-(2,6,6-trimethyl-cyclohex-1-enyl)-3,7-dimethyl-nona-2,4,6,8-tetraenal

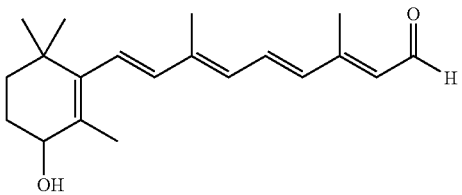 [SMILES: CC1=C(/C=C/C(C)=C/C=C/C(C)=C/C=O)C(C)(C)CCC1O]

2 g (5.37 mmol) of the tert-butyl ester of hydroxy retinoic acid, prepared according to step 3 of example 4, was placed in solution in 10 volumes of toluene under nitrogen flux and out of direct light. The medium was cooled to −78° C. then 4.57 ml (5.48 mmol) of a 20% Dibal-H solution in toluene was added drop by drop. After 3 h of stirring at −78° C., 20 volumes of a saturated solution of Rozen salts was added. The medium was extracted with toluene, the organic phases were washed in a saturated NaCl solution, dried on MgSO4, filtered and concentrated under vacuum. The crude product obtained was purified on a silica column and eluted on a heptane/ethyl acetate 9/1 gradient. 180 mg of a yellow solid was obtained (20%).

Rf=0.2 (heptane/ethyl acetate 7/3)

Mass spectrometry: [M+Na+]=323 (calculated [MH+] 300)

Step 2

9-[(3-trans decenoate)-2,6,6 trimethyl-cyclohex-1-enyl]-3,7-dimethyl-nona-2,4,6,8 tetraenal

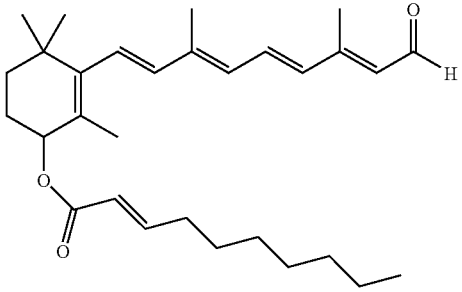 [SMILES: CCCCCCC/C=C/C(=O)OC1CCC(C)(C)C(/C=C/C(C)=C/C=C/C(C)=C/C=O)=C1C]

0.3 g (1 mmol) of the compound of step 1 was placed in solution in 30 volumes of dichloromethane at 0° C. 0.14 g (1.15 eq) of dimethylaminopyridine was added as well as 1.1 eq of trans-2-decanoic acid. 0.24 g of dicyclohexylcarbodiimide was added and the reaction mixture was stirred for 24 h at room temperature. The medium was filtered on celite to remove urea salts and the filtrate was concentrated. Purification by silica chromatography gave the expected product.

Rf=0.7 (heptane/ethyl acetate 7/3)

Mass spectrometry: [MNa+] 475 (calculated [MH+] 452)

EXAMPLE 9

9-[(3 oleate)-2,6,6-trimethyl-cyclohex-1-enylf]-3,7-dimethyl-nona-2,4,6,8 tetraenal

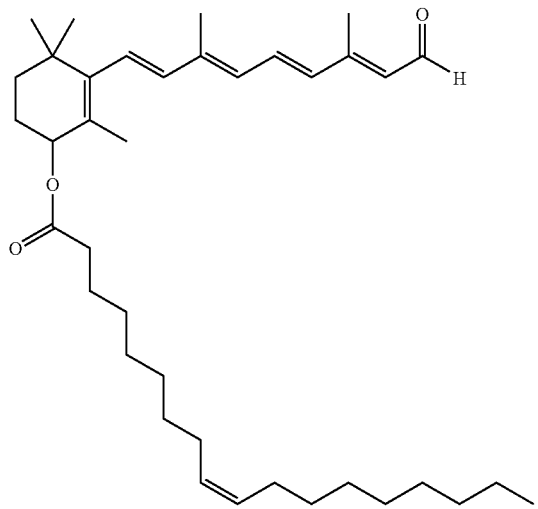 [SMILES: CCCCCCCC/C=C\CCCCCCCC(=O)OC1CCC(C)(C)C(/C=C/C(C)=C/C=C/C(C)=C/C=O)=C1C]

0.3 g (1 mmol) of the compound of example 7, step 1, was placed in solution in 30 volumes of dichloroethane. 0.09 ml (1 eq) of pyridine was added. This was followed by slow addition of 1.1 eq of the oleyl chloride derivative to the reaction medium. The medium was stirred for 7 h at room temperature. The medium was hydrolysed and extracted with dichloroethane. The organic phases were washed in a saturated NaCl solution then in a 0.1M HCl solution and finally in a saturated NaCl solution. After drying on $Na_2SO_4$ and filtration, the organic phases were concentrated under vacuum. The crude product was purified by silica chromatography to yield the expected product.

Rf=0.7 (heptane/ethyl acetate 7/3)

Mass spectrometry: [MNa⁺] 587 (calculated [MH⁺] 564)

EXAMPLE 10

9-[(3-linoleate)-2,6,6-trimethyl-cyclohex-1-enyl]-3,7-dimethyl-nona-2,4,6,8 tetraenal

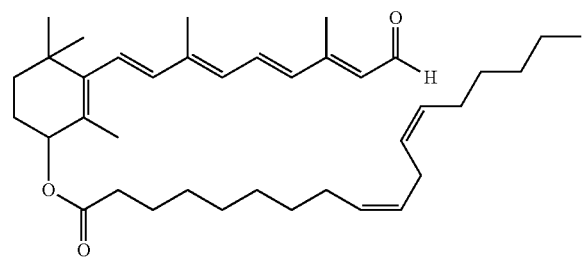 [SMILES: CCCCC/C=C\C/C=C\CCCCCCCC(=O)OC1CCC(C)(C)C(/C=C/C(C)=C/C=C/C(C)=C/C=O)=C1C]

The expected product was obtained using a method identical to that described in example 8 but replacing oleyl chloride with linoleyl chloride.

EXAMPLE 11

9-[(3-lipoate)-2,6,6-trimethyl-cyclohex-1-enyl]-3,7-dimethyl-nona-2,4,6,8-tetraenal

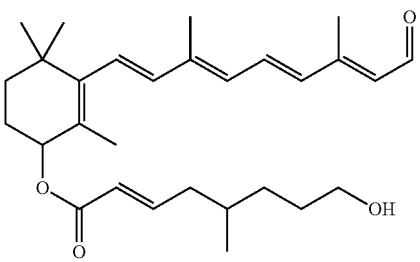 [SMILES: CC1=C(/C=C/C(C)=C/C=C/C(C)=C/C=O)C(C)(C)CCC1OC(=O)/C=C/CC(C)CCCO]

The expected product was obtained using a method identical to that described in example 8 but replacing oleyl chloride with lipoyl chloride.

EXAMPLE 12

9[{3-(8-hydroxy-5-methyl-2-octenoate)}-2,6,6-trimethyl-cyclohex-1-enyl]-3,7-dimethyl-nona-2,4,6,8-tetraenal

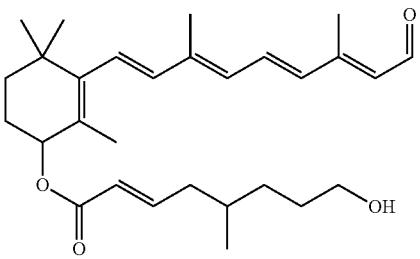 [SMILES: CC1=C(/C=C/C(C)=C/C=C/C(C)=C/C=O)C(C)(C)CCC1OC(=O)/C=C/CC(C)CCCO]

The expected product was obtained using a method identical to that described in example 8 but replacing oleyl chloride with the chloride of 8-hydroxy-5-methyl-2-octenoic acid.

EXAMPLE 13

9-[(3-tetraacetyl glucose)-2,6,6-trimethyl-cyclohex-1-enyl]-3,7-dimethyl-nona-2,4,6,8-tetraenal

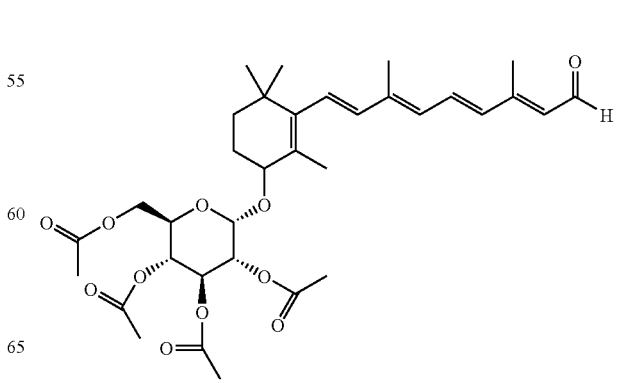

8 ml (2.5 eq) of a 1.0M $ZnCl_2$ a solution in ether was diluted in 2 volumes of toluene and 2 volumes of acetonitrile in the presence of 0.7 g molecular sieve 4Å. After stirring for 10 min, the reaction medium was plunged in a 90° C. bath and 0.21 g (0.70 mmol, 1 eq) of the compound of example 7, step 1, was added. After stirring for 10 min, 0.32 g (0.77 mmol, 1.1 eq) de 2,3,4,6-tetra-O-acetyl-alpha-D-glucopyranosylbromide and 0.25 ml (1.75 mmol, 2.5 eq) of triethylamine were added. The reaction medium was heated overnight at 80° C. The medium was filtered at room temperature and the filtrate was stirred in a saturated $NaHCO_3$ solution. After extraction and washing in a saturated NaCl solution, the organic phases were concentrated under vacuum. The crude product was purified by silica chromatography to yield the expected compound.

Rf=0.7 (heptane/ethyl acetate 7/3)

Mass spectrometry: $[M+Na^+]$=653 ($[M+H]^+$ calculated 630)

EXAMPLE 14

3-((1E,3E,5E,7E)-3,7-dimethyl-9-oxo-nona-1,3,5,7-tetraenyl)-2,4,4-trimethyl-cyclohex-2-enyl ester of (9Z,12Z,15Z)-Octadeca-9,12,15-trienoic acid

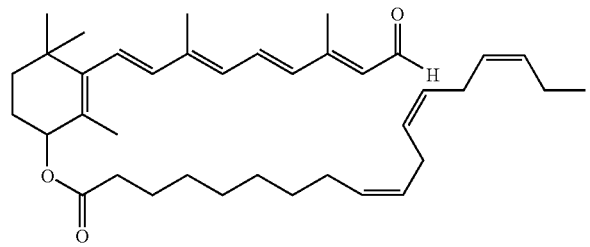 [SMILES: CC/C=C\C/C=C\C/C=C\CCCCCCCC(=O)OC1CCC(C)(C)C(/C=C/C(C)=C/C=C/C(C)=C/C=O)=C1C]

In dry Tricol under nitrogen reflux, out of direct light, 0.25 g (0.83 mmol) of Hydroxy-retinal was placed in solution with 35 volumes of Dichloromethane. 0.28 g (1.2 eq) of linolenic acid was added to the medium as well as 0.13 g (1 eq) of dimethylaminopyridine. Dicyclohexylcarbodiimide (0.20 g, 1 eq) in 5 volumes of Dichloromethane was poured in slowly. The reaction medium was stirred overnight at room temperature. TLC screening made it possible to regulate the reaction endpoint. The medium was then filtered and concentrated under vacuum. The residue was purified on a silica column, out of direct light, then eluted on a heptane/ethyl acetate gradient to yield a yellow solid (0.40 g, i.e. a yield of about 85%).

TLC (Heptane/ethyl acetate 7/3): Rf=0.8

Mass spectrometry: $[M+Na]^+$=583 (calculated 560)

EXAMPLE 15

3-((1E,3E,5E,7E)-3,7-dimethyl-9-oxo-nona-1,3,5,7-tetraenyl)-2,4,4-trimethyl-cyclohex-2-enyl ester of (9Z,12Z)-Octadeca-9,12-dienoic acid

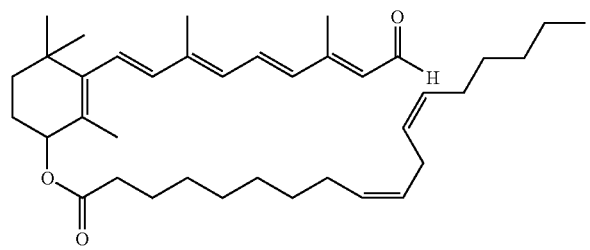 [SMILES: CCCCC/C=C\C/C=C\CCCCCCCC(=O)OC1CCC(C)(C)C(/C=C/C(C)=C/C=C/C(C)=C/C=O)=C1C]

The same operating conditions as in example 13 are applied to Hydroxyretinal and linolenic acid in order to carry out esterification on a 250 mg scale with a yield of 34%.

EXAMPLE 16

3-((1E,3E,5E,7E)-3,7-dimethyl-9-oxo-nona-1,3,5,7-tetraenyl)-2,4,4-trimethyl-cyclohex-2-enyl ester of (E)-14-Hydroxy-tetradec-2-enoic acid

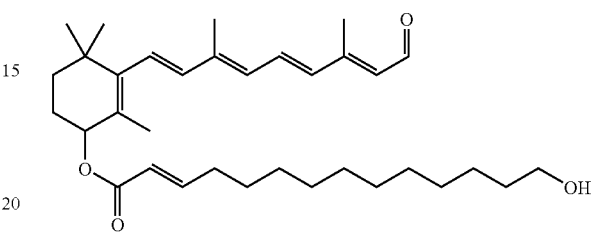

The same operating conditions for protection-esterification-deprotection are applied to Hydroxyretinal and (E)-14-tetradec-2-enoic acid (synthesized in advance) on a 500 mg gradient with an overall yield of 15%.

TLC (Heptane/ethyl acetate 7/3): Rf=0.2

Mass spectrometry: $[M+Na]^+$=547 (calculated 524)

EXAMPLE 17

3-((1E,3E,5E,7E)-3,7-dimethyl-9-oxo-nona-1,3,5,7-tetraenyl)-2,4,4-trimethyl-cyclohex-2-enyl ester of (E)-10-Acetoxy-dec-2-enoic acid

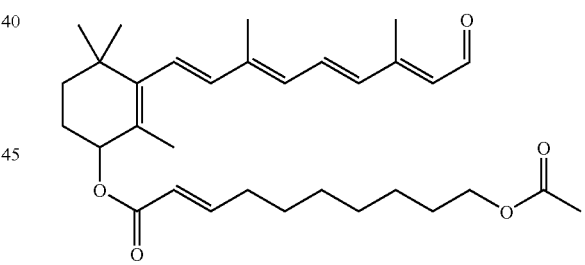

In dry Tricol under nitrogen reflux, 1 g (5.3 mmol) of (E)-10-Hydroxy-dec-2-enoic acid was dissolved in 10 volumes of pyridine. 546 µl (1.1 eq) of acetic anhydride was poured on. The reaction medium was stirred at room temperature overnight. TLC screening made it possible to regulate the reaction endpoint. The medium was then filtered and concentrated under vacuum. The residue was taken up in a brine and ethyl acetate solution. The mixture was extracted with ethyl acetate and the organic phases washed in 1M hydrochloric acid, followed by a saturated NaCl solution then dried on $MgSO_4$, filtered and concentrated under vacuum to yield a brown oil. The crude product was purified on a silica column and eluted on a heptane/ethyl acetate gradient. 850 mg of a yellow oil was obtained (70% yield).

In dry Tricol under nitrogen reflux, 0.25 g (0.83 mmol, 1.2 eq) of hydroxyretinol yellow crystals was placed in solution in 40 volumes of dichloromethane. The protected hydroxy-acid in acetate form (0.25 g, 1 eq) was diluted in 40 volumes of Dichloromethane and poured on the reaction medium. 0.15 g (1 eq) of Dimethylaminopyridine was added then Dicyclohexylcarbodiimide (0.38 g, 1.2 eq) dissolved in 20 volumes of Dichloromethane was poured slowly onto the reaction medium. The mixture was stirred out of direct light overnight. TLC screening made it possible to regulate the reaction end-point. The reaction medium was then filtered and the filtrate was concentrated. The residue obtained was purified on a silica column then eluted on a heptane/ethyl acetate gradient, out of direct light. 0.28 g of a yellow oil was obtained (65% yield).

TLC (Heptane/ethyl acetate 7/3): Rf=0.4 regulate the deprotection end-point. The medium was hydrolysed by addition of water. It was then extracted with dichloromethane. The organic phases were collected, washed in a saturated NaCl solution, dried on $MgSO_4$, filtered and concentrated. The residue was purified on a silica gel column and eluted on a heptane/ethyl acetate gradient, out of direct light. 0.11 g of a yellow solid was obtained, giving a yield of 60%.

TLC (Heptane/ethyl acetate 7/3): Rf=0.2

Mass spectrometry: $[M+Na]^+$=491 (calculated 468)

EXAMPLE 19

3-((1E,3E,5E,7E)-3,7-dimethyl-9-oxo-nona-1,3,5,7-tetraenyl)-2,4,4-trimethyl-cyclohex-2-enyl and (R)-2,8-dimethyl-2-((4R,8R)-4,8,12-trimethyltridecyl)-1-benzopyran-6-yl bis ester heptanedioic acid

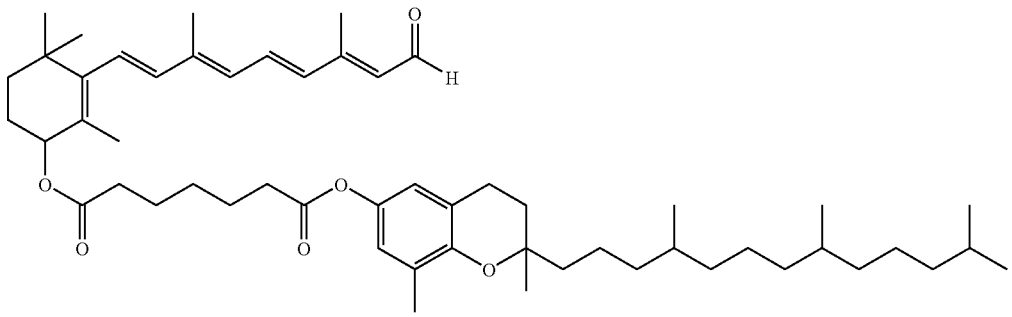

EXAMPLE 18

3-((1E,3E,5E,7E)-3,7-dimethyl-9-oxo-nona-1,3,5,7-tetraenyl)-2,4,4-trimethyl-cyclohex-2-enyl ester of (E)-10-Hydroxy-dec-2-enoic acid

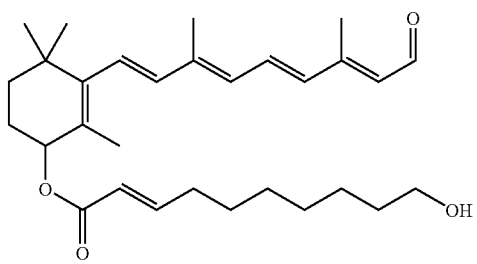 [SMILES: CC1=C(/C=C/C(C)=C/C=C/C(C)=C/C=O)C(C)(C)CCC1OC(=O)/C=C/CCCCCCCO]

The same procedure as in example 17 is followed then 0.2 g of the previous oil is diluted in 40 volumes of methanol in a flask. 467 μl of a freshly prepared solution of $KHCO_3$ and $K_2CO_3$ (respectively 70 mg and 50 mg in 1 ml of methanol) is added. The medium is stirred at room temperature out of direct light for 4 h30. TLC monitoring made it possible to In dry Tricol under nitrogen flux, 0.8 g (0.95 eq) of pimelic acid was placed in solution in 20 volumes of dichloromethane. 1.1 g (1 eq) of dicyclohexylcarbodiimide and 0.63 g (1 eq) of dimethylaminopyridine were added. After 5 minutes of stirring at room temperature, 2.1 g (5.2 mmol) of (+)-delta tocopherol in 10 volumes of dichloromethane was poured onto slowly. The reaction medium was stirred for 6 h. TLC monitoring made it possible to regulate the reaction end-point. The medium was then filtered and concentrated. The residue was purified on a silica gel column and eluted on a heptane/ethyl acetate gradient. 0.35 g of oil was obtained (yield 12%)

In dry Tricol under nitrogen flux, out of direct light, 0.17 g (0.57 mmol) of hydroxy-retinaldehyde was placed in solution in 30 volumes of dichloromethane, at 0° C. 0.08 g (1.2 eq) of dimethylaminopyridine was added as well as 0.35 g (1.15 eq) of a tocopherol-C7 spacer derivative obtained previously was added. 0.17 g (1.4 eq) of dicyclohexylcarbodiimide in 20 volumes of dichloromethane was poured onto the medium at 0° C., and the mixture stirred for 24 h at room temperature. TLC monitoring made it possible to regulate the reaction end-point. The medium was filtered on celite to remove urea salts and filtrate was concentrated. The crude product was purified by silica gel chromatography, out of direct light, to yield orange-yellow oil (0.28 g, i.e. a yield of 60%).

TLC (Heptane/ethyl acetate 7/3): $R_f$=0.5

Mass spectrometry: $[M+Na]^+$=849 (calculated 827)

EXAMPLE 20

3-((1E,3E,5E,7E)-3,7-dimethyl-9-oxo-nona-1,3,5,7-tetraenyl)-2,4,4-trimethyl-cyclohex-2-enyl and (R)-2,8-dimethyl-2-((4R,8R)-4,8,12-trimethyltridecyl)-1-benzopyran-6-yl bis ester nonanedioic acid

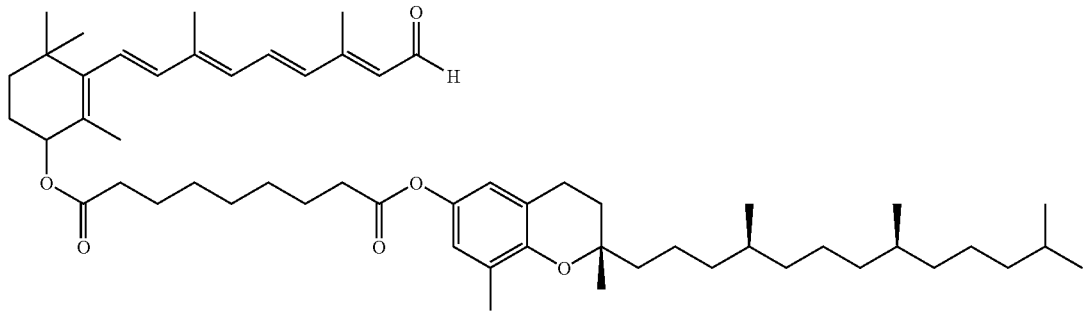 [SMILES: CC1=C(/C=C/C(C)=C/C=C/C(C)=C/C=O)C(C)(C)CCC1OC(=O)CCCCCCCC(=O)Oc1cc(C)c2c(c1)CC[C@](C)(CCC[C@@H](C)CCC[C@@H](C)CCCC(C)C)O2]

The same operating conditions as in the preceding example were applied to (+)-delta-tocopherol and azelaic acid. This derivative was then coupled to hydroxyretinal by esterification on a 250 mg scale with an overall yield of 11%.
TLC (Heptane/ethyl acetate 7/3): $R_f$=0.6
Mass spectrometry: $[M+Na]^+$=877 (calculated 854)

EXAMPLE 21

3-(1E,3E,5E,7E)-3,7-dimethyl-9-oxo-nona-1,3,5,7-tetraenyl)-2,4,4-trimethyl-cyclohex-2-enyl and (R)-2,8-dimethyl-2-((4R,8R)-4,8,12-trimethyltridecyl)-1-benzopyran-6-yl bis ester succinic acid

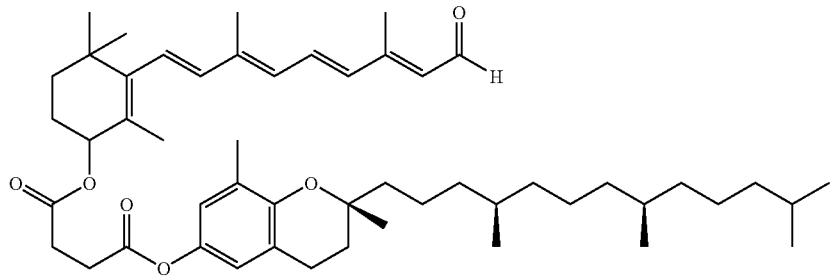 [SMILES: CC1=C(/C=C/C(C)=C/C=C/C(C)=C/C=O)C(C)(C)CCC1OC(=O)CCC(=O)Oc1cc(C)c2c(c1)CC[C@@](C)(CCC[C@H](C)CCC[C@H](C)CCCC(C)C)O2]

The same operating conditions as previously were applied to (+)-delta tocopherol and succinic acid. This derivative was then coupled to hydroxyretinal by esterification on a 200 mg scale with an overall yield of 3%.
TLC (Heptane/ethyl acetate 7/3): $R_f$=0.5

EXAMPLE 22

3-((1E,3E,5E,7E)-3,7-dimethyl-9-oxo-nona-1,3,5,7-tetraenyl)-2,4,4-trimethyl-cyclohex-2-enyl and (R)-2,8-dimethyl-2-((4R,8R)-4,8,12-trimethyltridecyl)-1-benzopyran-6-yl bis ester of pentanedioic acid

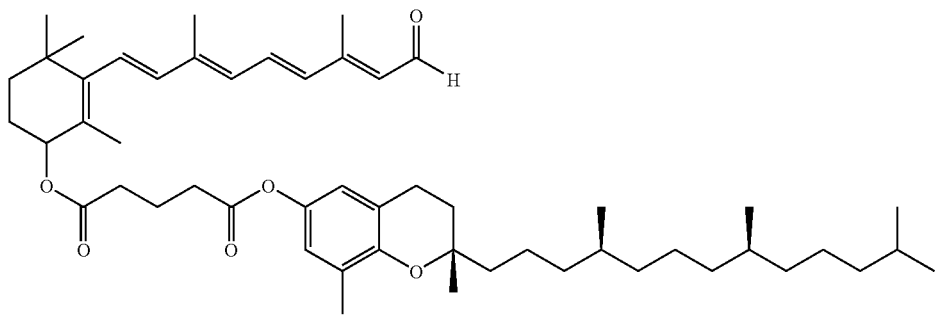 [SMILES: CC1=C(/C=C/C(C)=C/C=C/C(C)=C/C=O)C(C)(C)CCC1OC(=O)CCCC(=O)Oc1cc(C)c2c(c1)CC[C@](C)(CCC[C@@H](C)CCC[C@@H](C)CCCC(C)C)O2]

The same operating conditions as previously were applied to (+)-delta tocopherol and glutaric acid. This derivative was then coupled to hydroxyretinal by esterification on a 250 mg scale with an overall yield of 21%.
TLC (Heptane/ethyl acetate 7/3): $R_f$=0.6

EXAMPLE 23

| Whitening composition | |
| --- | --- |
| Composition (O/W emulsion) | Quantity (g) |
| Compound of example 3 | 0.1 |
| Vaseline | 8 |
| Glycerine 99.5% | 15 |
| Glyceryl stearate GS | 5 |
| Stearic acid | 3 |

-continued

| Whitening composition | |
| --- | --- |
| Composition (O/W emulsion) | Quantity (g) |
| Liquid paraffin 352 | 4 |
| Cyclop entasiloxane | 3 |
| Macrogol 600 | 5 |
| Ethanolamine (tri) | 0.5 |

| Whitening composition | |
|---|---|
| Composition (O/W emulsion) | Quantity (g) |
| Paraben | 0.4 |
| Purified water | QS for 100 |

| Whitening lotion | |
|---|---|
| Composition | Quantity (g) |
| Compound of example 3 | 0.1 |
| Betaine cocamidopropyl B4F | 2 |
| Macrogol 600 | 4 |
| Phenylethyl alcohol | 0.5 |
| Ethanolamine (tri) | 0.04 |
| Purified water | QS for 100 |

The invention claimed is:

1. Compound of formula (I):

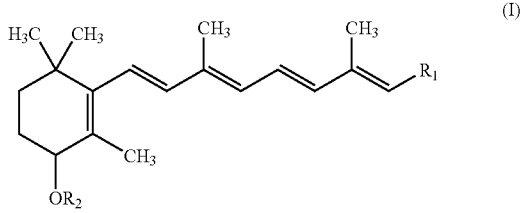

(I)

wherein $R_1$ represents a $R'_1$ or -A-$R'_1$ group in which $R'_1$ is chosen from among —COOH, —COOR$_3$, —CONH$_2$, —CONHR$_3$, —CONR$_3$R$_4$, —CHO, —CH$_2$OH, —CH$_2$OR$_5$, and A represents a linear or branched $C_1$-$C_{16}$ alkylene group, linear or branched $C_2$-$C_{16}$ alkenylene group or linear or branched $C_2$-$C_{16}$ alkynylene group $R_2$ represents:

an aryl group, optionally substituted, or heteroaryl group, optionally substituted, or an osidic residue, or a linear or branched fatty acid with 4 to 30 carbon atoms, -an —OC—(CH$_2$)$_n$—CO-tocopheryl (alpha, beta or gamma or delta) group with $2 \leq n \leq 10$, an —R'$_2$—O—R$_6$ group, wherein R'$_2$ is an arylene group, optionally substituted, or a heteroarylene group, optionally substituted, and R$_6$ represents hydrogen atom, linear or branched $C_1$-$C_{16}$ alkyl groups, optionally substituted, linear or branched $C_2$-$C_{16}$ alkenyl group, optionally substituted, linear or branched $C_2$-$C_{16}$ alkynyl group, optionally substituted, a tocopheryl radical, optionally substituted, or an amino acid residue $R_3$ and $R_4$ independently represent a linear or branched $C_1$-$C_{16}$ alkyl radical, optionally substituted, linear or branched $C_2$-$C_{16}$ alkenyl, or linear or branched $C_2$-$C_{16}$ alkynyl, optionally substituted, $R_5$ represents a linear or branched $C_1$-$C_{16}$ alkyl radical, optionally substituted, linear or branched $C_2$-$C_{16}$ alkenyl group, optionally substituted, branched or linear $C_2$-$C_{16}$ alkynyl group optionally substituted or a linear or branched $C_2$-$C_{16}$ acyl group, optionally substituted, their enantiomers and diastereoisomers, as well as any salts resulting from addition to an acid or physiologically acceptable base.

2. Compound of formula (I) according to claim 1 wherein $R_1$ represents a group chosen from among —COOH, —COOR$_3$, —CHO, —CH$_2$OH, —CH$_2$OR$_5$ wherein R$_3$ and R$_5$ are as defined in claim 1.

3. Compound of formula (I) according to claim 1 wherein A represents a methylene group.

4. Compound of formula (I) according to claim 1 wherein $R_2$ represents an —R'$_2$—O —R$_6$ group in which R'$_2$ is an arylene group, optionally substituted, and R$_6$ represents a linear or branched ($C_1$-$C_6$) alkyl group.

5. Compound of formula (I) according to claim 1 characterized in that it is chosen from among:

(2E,4E,6E,8E)-3,7-dimethyl-9-{2,6,6-trimethyl-3-[4-((2S,3R,4S,5S,6R)-3,4,5-trihydroxy-6-hydroxymethyl-tetrahydro-pyran-2-yloxy)-phenoxy]-cyclohex-1-enyl}-nona-2,4,6,8-tetraenoic acid, tert-butyl ester of (2E,4E,6E,8E)-9-[3-(4-methoxy-phenoxy)-2,6,6-trimethyl-cyclohex-1-enyl]-3,7-dimethyl-nona-2,4,6,8-tetraenoic acid, (2E,4E,6E,8E)-9-[3-(4-methoxy-phenoxy)-2,6,6-trimethyl-cyclohex-1-enyl]-3,7-dimethyl-nona-2,4,6,8-tetraenal, tert-butyl ester of (2E,4E,6E,8E)-9-[3-(4-hydroxy-phenoxy)-2,6,6-trimethyl-cyclohex-1-enyl]-3,7-dimethyl-nona-2,4,6,8-tetraenoic acid, (2E,4E,6E,8E)-9-[3-(4-hydroxy-phenoxy)-2,6,6-trimethyl-cyclohex-1-enyl]-3,7-dimethyl-nona-2,4,6,8-tetraenal, 9-[(3-trans decenoate)-2,6,6 trimethyl-cyclohex-1-enyl]-3,7-dimethylnona-2,4,6,8 tetraenal, 9-[(3-linoleate)-2,6,6-trimethyl-cyclohex-1-enyl]-3,7-dimethyl-nona-2,4,6,8-tetraenal, 9-[(3-linolenate)-2,6,6-trimethyl-cyclohex-1-enyl]-3,7-dimethylnona-2,4,6,8-tetraenal, 3-((lE,3E,5E,7E)-3,7-dimethyl-9-oxo-nona-1,3,5,7-tetraenyl)-2,4,4-trimethyl-cyclohex-2-enyl ester of (9Z, 12Z,15Z)-Octadeca-9,12,15-trienoic acid 9-[(3-lipoate)-2,6,6-trimethyl-cyclohex-1-enyl]-3,7-dimethyl-nona-2,4,6,8-tetraenal, 9-[{3-(8-hydroxy-5-methyl-2-octenoate)}-2,6,6-trimethyl-cyclohex-1-enyl]-3,7-dimethyl-nona-2,4,6,8-tetraenal, 3-((1E,3E,5E,7E)-3,7-dimethyl-9-oxo-nona-1,3,5,7-tetraenyl)-2,4,4-trimethyl-cyclohex-2-enyl ester of (E)-14-Hydroxy-tetradec-2-enoic acid, 3-((1E,3E,5E,7E)-3,7-dimethyl-9-oxo-nona-1,3,5,7-tetraenyl)-2,4,4-trimethyl-cyclohex-2-enyl ester of (EH 0-Hydroxy-dec-2-enoie acid, 3-((1E,3E,5E,7E)-3,7-dimethyl-9-oxo-nona-1,3,5,7-tetraenyl)-2,4,4-trimethyl-cyclohex-2-enyl ester of (E)--10-Acetoxy-dec-2-enoic acid, 9-[(3-tetraacetyl glucose)-2,6,6-trimethyl-cyclohex-1-enyl]-3,7-dimethyl-nona-2,4,6,8-tetraenal, 3-((1E,3E,5E,7E)-3 ,7-dimethyl-9-oxo-nona- 1,3,5,7-tetraenyl)-2,4,4-trimethyl-cyclohex-2-enyl and (R)-2,8-dimethyl-2-((4R, 8R)-4,8,12-trimethyltridecyl)-1-benzopyran-6-yl bis ester of heptanedioic acid, 3-((1E,3E,5E,7E)-3,7-dimethyl-9-oxo-nona-1,3,5,7-tetraenyl)-2,4,4-trimethyl-cyclohex-2-enyl and (R)-2,8-dimethyl-24(4R,8R)-4,8,12-trimethyltridecyl)- 1-benzopyran-6-yl bis ester of nonanedioic acid, 3-((1E,3E,5E,7E)-3,7-dimethyl-9-oxo-nona-1,3,5,7-tetraenyl)-2,4,4-trimethyl-cyclohex-2-enyl and (R)-2,8-dimethyl-2-((4R,8R)-4,8,1 2-trimethyltridecyl)- 1-benzopyran-6-yl bis ester of succinic acid, or 3-((1 E,3 E,5E,7E)-3 ,7-dimethyl-9-oxo-nona-1 ,3 ,5,7-tetraenyl)-2,4,4-trimethyl-cyclohex-2-enyl and (R)-2,8- dimethyl-2-((4R,8R)-4,8,12-trimethyltridecyl)- 1-benzopyran-6-yl bis ester of pentanedioic acid.

6. Method for the preparation of compounds of formula (I) according to claim 1 characterized in that the compound of formula (II):

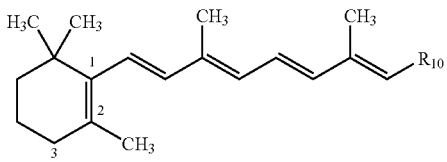

wherein $R_{10}$ has the same meaning as the $R_1$ radical according to claim 1, with the exception of the —CH$_2$OH group, undergoes an allylic oxidation reaction in position 3 to yield a compound of formula (III):

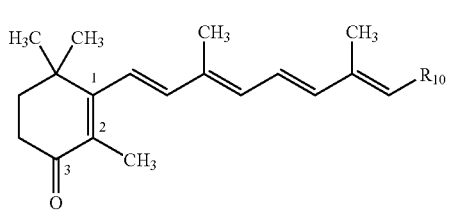

wherein $R_{10}$ is as defined previously,
whose carbonyl group in position 3 is then reduced to the corresponding alcohol of formula (IV):

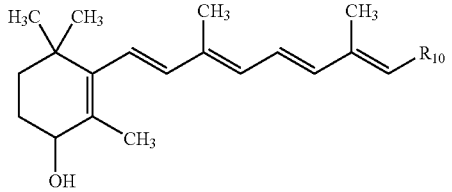

compound (IV) undergoes an alkylation reaction or coupling reaction in alkaline, acid or neutral medium, possibly in the presence of a coupling reagent, using a reagent of formula $R_2$—X wherein X represents a hydroxy group or a halogen atom, it being understood that the hydroxy group can be activated in the form of a starting group, if need be, to yield a compound of formula (Ia):

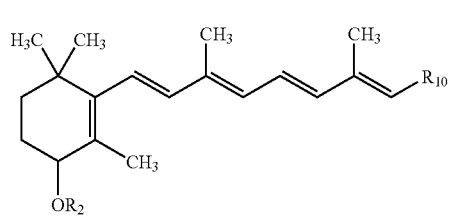

particular case of compounds of formula (I) wherein $R_2$ is as defined in claim 1, and $R_{10}$ has the same meaning as previously, which, when the $R_{10}$ radical represents a —COOR$_3$ group as defined in claim 1, can undergo a hydrolysis or reduction reaction to yield a compound of formula (Ib):

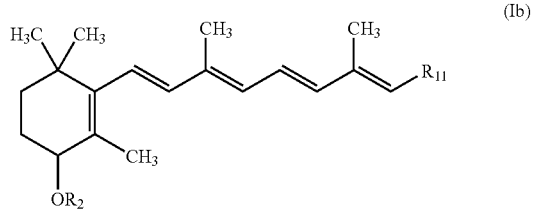

particular case of compounds of formula (I) wherein $R_2$ is as defined in claim 1, and $R_{11}$ represents a —COOH or CH$_2$OH group,
it being understood that the different groups present in the preceding compounds are suitable for the synthesis of protected then deprotected groups at any time, depending on their incompatibility with the reagents used.

7. Compound of formula (IIIa):

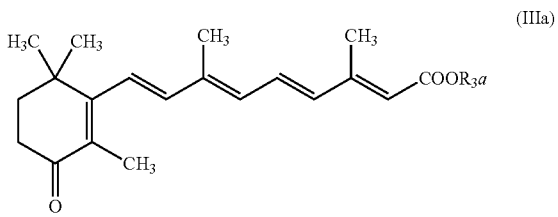

wherein the $R_3a$ group represents a branched $C_3$-$C_{16}$ alkyl group.

8. Tert-butyl ester of (2E,4E,6E,8E)-9-(3-oxo-2,6,6-trimethyl-cyclohex-1-enyl)-3,7-dimethyl-nona-2,4,6,8-tetranoic acid of formula (IIIa) according to claim 7.

9. Compound of formula (IVa):

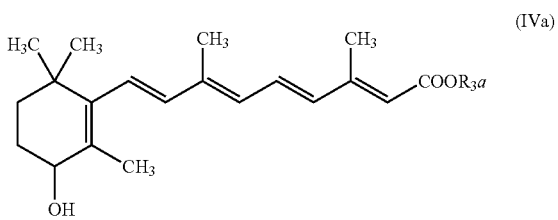

wherein the $R_3a$ group represents a branched $C_3$-$C_{16}$ alkyl group.

10. Tert-butyl ester of (2E,4E,6E,8E)-9-(3-Hydroxy-2,6,6-trimethyl-cyclohex-1-enyl)-3,7-dimethyl-nona-2,4,6,8-tetraenoic acid of formula IVa according to claim 9.

11. Cosmetic or dermatological composition characterized in that it contains at least one compound of formula (I) according to claim 1 in a physiologically acceptable medium.

12. Composition according to claim 11 characterized in that the amount of compound of formula (I) ranges from 0.01% to 5% by weight with respect to the total weight of the composition.

13. Method for whitening and/or lightening human skin and/or body hair and/or head hair, which comprises applying to the skin and/or body hair and/or head hair of a cosmetic composition containing at least one compound of formula (I) according to claim 1.

14. Method of depigmenting skin and/or body hair and/or head hair which comprises administering to a patient an effective amount of a dermatological composition containing at least one compound of formula (I) according to claim 1.

15. A medication comprising at least one compound formula (I) according to claim 1.

16. A method for depigmenting the skin, which comprises administering to a patient an effective amount of a composition containing at least one compound of formula (I) according to claim 1.

17. The compound of claim 1, wherein $R_2$ represents a fatty acid, which is branched and/or substituted at the end of the chain.

18. The compound of claim 17, wherein the fatty acid is substituted at the end of the chain by a hydroxy, acetoxy or protected or non-protected amino radical.

* * * * *